US009233923B2

(12) United States Patent
Kim et al.

(10) Patent No.: US 9,233,923 B2
(45) Date of Patent: Jan. 12, 2016

(54) ORGANIC COMPOUNDS FOR ORGANIC ELECTRONIC DEVICES AND TERMINALS

(75) Inventors: Dongha Kim, Seongnam-si (KR); Wonsam Kim, Seongnam-si (KR); Daesung Kim, Yongin-si (KR); Daehyuk Choi, Suwon-si (KR); Junghwan Park, Seoul (KR); Jungcheol Park, Jinhae-si (KR); Kiwon Kim, Incheon (KR); Hwasoon Jung, Chuncheon-si (KR); Yongwook Park, Anyang-si (KR); Hansung Yu, Anyang-si (KR); Soungyun Mun, Yongin-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 383 days.

(21) Appl. No.: 13/262,479

(22) PCT Filed: Mar. 29, 2010

(86) PCT No.: PCT/KR2010/001905
§ 371 (c)(1),
(2), (4) Date: Sep. 30, 2011

(87) PCT Pub. No.: WO2010/114267
PCT Pub. Date: Oct. 7, 2010

(65) Prior Publication Data
US 2012/0018717 A1 Jan. 26, 2012

(30) Foreign Application Priority Data

Mar. 30, 2009 (KR) .................. 10-2009-0026838
May 7, 2009 (KR) .................. 10-2009-0039878
Jun. 5, 2009 (KR) .................. 10-2009-0050078
Jun. 22, 2009 (KR) .................. 10-2009-0055429

(51) Int. Cl.
| H01L 51/54 | (2006.01) |
| C09K 11/06 | (2006.01) |
| C07D 401/04 | (2006.01) |
| C07D 403/04 | (2006.01) |
| C07D 471/04 | (2006.01) |
| C07D 403/10 | (2006.01) |
| C07D 209/56 | (2006.01) |
| C07D 401/10 | (2006.01) |
| C07D 209/86 | (2006.01) |
| C07D 209/94 | (2006.01) |
| H01L 51/00 | (2006.01) |
| H05B 33/14 | (2006.01) |
| C09B 57/00 | (2006.01) |
| C07D 403/08 | (2006.01) |
| H01L 51/50 | (2006.01) |

(52) U.S. Cl.
CPC ............ *C07D 209/86* (2013.01); *C07D 209/94* (2013.01); *C07D 401/04* (2013.01); *C07D 403/04* (2013.01); *C07D 403/08* (2013.01); *C09B 57/00* (2013.01); *C09B 57/008* (2013.01); *C09K 11/06* (2013.01); *H01L 51/006* (2013.01); *H01L 51/0072* (2013.01); *H05B 33/14* (2013.01); *C09K 2211/1029* (2013.01); *C09K 2211/1044* (2013.01); *C09K 2211/1059* (2013.01); *H01L 51/5012* (2013.01); *Y02E 10/549* (2013.01)

(58) Field of Classification Search
None
See application file for complete search history.

(56) References Cited

U.S. PATENT DOCUMENTS

| 5,705,511 | A |  | 1/1998 | Hudkins et al. |
| 5,942,340 | A | * | 8/1999 | Hu et al. .................. 428/690 |
| 6,399,780 | B1 |  | 6/2002 | Hudkins |
| 7,521,525 | B2 |  | 4/2009 | Sohn et al. |
| 8,361,638 | B2 |  | 1/2013 | Stoessel et al. |
| 2002/0071963 | A1 | * | 6/2002 | Fujii .......................... 428/690 |
| 2002/0074936 | A1 | * | 6/2002 | Yamazaki et al. ......... 313/504 |
| 2005/0221124 | A1 |  | 10/2005 | Hwang et al. |
| 2006/0063033 | A1 |  | 3/2006 | Sohn et al. |
| 2007/0042220 | A1 | * | 2/2007 | Inoue et al. ............... 428/690 |
| 2007/0257600 | A1 | * | 11/2007 | Matsuura et al. ......... 313/498 |
| 2008/0124455 | A1 |  | 5/2008 | Shin et al. |
| 2008/0220285 | A1 | * | 9/2008 | Vestweber et al. ....... 428/690 |
| 2009/0295276 | A1 | * | 12/2009 | Asari et al. ............... 313/504 |
| 2009/0302743 | A1 | * | 12/2009 | Kato et al. ............... 313/504 |
| 2011/0037027 | A1 | * | 2/2011 | Stoessel et al. ......... 252/301.16 |
| 2011/0272685 | A1 |  | 11/2011 | Parham et al. |

FOREIGN PATENT DOCUMENTS

| CN |  | 1370173 | A | 9/2002 |
| CN |  | 1749295 | A | 3/2006 |
| CN |  | 102272264 | A | 12/2011 |
| DE | 1 0 2009 005 288 | A1 |  | 7/2010 |
| JP |  | 08012430 | B2 | 2/1996 |

(Continued)

OTHER PUBLICATIONS

Extended European Search Report for Application No. EP 10 75 8992 dated Mar. 22, 2013 (7 pages).
Japanese Office Action for Application No. 2012-501944 dated Jun. 3, 2013 (5 pages).
Wise, Stephen A. et al., "Characterization of Polycyclic Aromatic Hydrocarbon Minerals Curtisite, Idrialite and Pendletonite Using High-Performance Liquid Chromatography, Gas Chromatography, Mass Spectrometry and Nuclear Magnetic Resonance Spectroscopy", Chemical Geology, 54 (1986), pp. 339-357.

(Continued)

*Primary Examiner* — Andrew K Bohaty
(74) *Attorney, Agent, or Firm* — Vorys, Sater, Seymour and Pease LLP; Mihsun Koh

(57) ABSTRACT

Organic compounds, and organic electronic devices and terminals that include the organic compounds, are disclosed. The organic compounds have aryl or hetero aryl groups condensed with inden and indole groups. When included in an organic electronic device or terminal, the organic compound improves the luminous efficiency, the stability, and the lifetime of the organic electronic device or terminal.

19 Claims, 6 Drawing Sheets

(56) References Cited

FOREIGN PATENT DOCUMENTS

| | | |
|---|---|---|
| JP | 09310066 A | 12/1997 |
| JP | 2001-509775 A | 7/2001 |
| JP | 2006-083386 A | 3/2006 |
| JP | 2011-521894 A | 7/2011 |
| KR | 1020050097670 A | 10/2005 |
| WO | WO-01-14380 A1 | 3/2001 |
| WO | WO 2007063796 A1 * | 6/2007 |
| WO | WO-2008-062636 A1 | 5/2008 |
| WO | WO-2009-124627 A1 | 10/2009 |
| WO | WO 2009124627 A1 * | 10/2009 |

OTHER PUBLICATIONS

Hudkins, Robert L. et al., "Fused Pyrrolo [2, 3-*c*] Carbazol-6-Ones; Novel Immunostimulants That Enhance Human Interferon- $\gamma$ Activity", Departments of Medicinal Chemistry and Call Bilogy, West Chester, PA, Journal of Medicinal Chemistry, 1997, vol. 40, No. 19, Mar. 26, 1997, pp. 2994-2996.

Chinese Office Action for Application No. 2010 80015465.4 dated Jun. 3, 2013 (6 pages).

* cited by examiner

ORGANIC COMPOUNDS FOR ORGANIC ELECTRONIC DEVICES AND TERMINALS

CROSS-REFERENCE TO RELATED APPLICATIONS

This is a U.S. National Stage Application of International application No. PCT/KR2010/001905, filed on Mar. 29, 2010 and published in the Korean language as WO 2010/114267 A2 on Oct. 7, 2010. This application claims priority from and the benefit under 35 U.S.C. §119(a) of Korean Patent Application No. 10-2009-0026838, filed on Mar. 30, 2009, No. 10-2009-0039878, filed May 7, 2009, No. 10-2009-0050078, filed on Jun. 5, 2009, and No. 10-2009-0055429, filed on Jun. 22, 2009, The disclosures of which are hereby incorporated by reference for all purposes as if fully set forth herein.

BACKGROUND OF THE INVENTION

1. Field of the Invention

The present invention relates to an organic electronic device and a compound thereof, and a terminal.

2. Description of the Prior Art

As generally known in the art, an organic light emitting phenomenon indicates conversion of electric energy into light energy by means of an organic material. An organic electronic device using the organic light emitting phenomenon generally has a structure including an anode, a cathode, and an organic material layer interposed therebetween. Herein, in many cases, the organic material layer may have a multi-layered structure having respective different materials in order to improve efficiency and stability of an organic electronic device. For example, it may include a hole injection layer, a hole transport layer, a light emitting layer, an electron transport layer, an electron injection layer, and the like.

Materials used as an organic material layer in an organic electronic device may be classified into a light emitting material and a charge transport material, for example, a hole injection material, a hole transport material, an electron transport material, an electron injection material, etc. according to their functions. Then, the light emitting material may be divided into a high molecular weight type and a low molecular weight type according to their molecular weight, and may be divided into a fluorescent material from electronic singlet excited states and a phosphorescent material from electronic triplet excited states according to their light emitting mechanism. Further, the light emitting material can be classified into a blue, green or red light emitting material and a yellow or orange light emitting material required for giving more natural color, according to a light emitting color.

Meanwhile, when only one material is used as a light emitting material, an efficiency of a device is lowered owing to a maximum luminescence wavelength being moved to a longer wavelength due to the interaction between the molecules, the deterioration of color purity and the reduction in light emitting efficiency. Therefore, a host/dopant system can be used as the light emitting material for the purpose of enhancing the color purity and the light emitting efficiency through energy transfer. It is based on the principle that if a small amount of a dopant having a smaller energy band gap than a host forming a light emitting layer is mixed with the light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according the kind of the dopant.

In order to allow the organic electronic device to fully exhibit the above-mentioned excellent characteristics, a material constituting the organic material layer in the device, for example, a hole injection material, a hole transport material, a light emitting material, an electron transport material and an electron injection material should be essentially composed of a stable and efficient material. However, the development of a stable and efficient organic material layer material for the organic electronic device has not yet been fully realized. Accordingly, the development of new materials is continuously desired.

SUMMARY OF THE INVENTION

The inventors of the present invention found a novel-structure compound having aryl or hetero aryl condensed with inden and indole. Also, they found that when the compound is applied to an organic electronic device, it is possible to significantly improve the luminous efficiency, the stability, and the lifetime of the device.

Accordingly, an object of the present invention is to provide a novel compound having aryl or hetero aryl condensed with inden and indole, an organic electronic device using the same, and a terminal including the device.

In accordance with an aspect of the present invention, there is provided a compound represented by Formula below:

The inventive compound having aryl or hetero aryl condensed with inden and indole may be used as a material for hole injection, hole transport, electron injection, electron transport, light emission, and passivation (capping) in an organic electronic device, and especially, may be used alone as a light emitting material, a host or a dopant in host/dopant, a hole injection layer, and a hole transport layer.

In an organic electronic device including the compound, it is possible to improve the efficiency, the lifetime and the stability, and to decrease the driving voltage, in the organic electronic device.

Accordingly, the present invention provides a compound having aryl or hetero aryl condensed with inden and indole, an organic electronic device using the same, and a terminal including the organic electronic device.

The inventive compound can perform various roles in an organic electronic device and a terminal. Further, when applied to the organic electronic device and the terminal, it can decrease the driving voltage of the device, and improve the luminous efficiency, the lifetime and the stability of the device.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Figure 1:
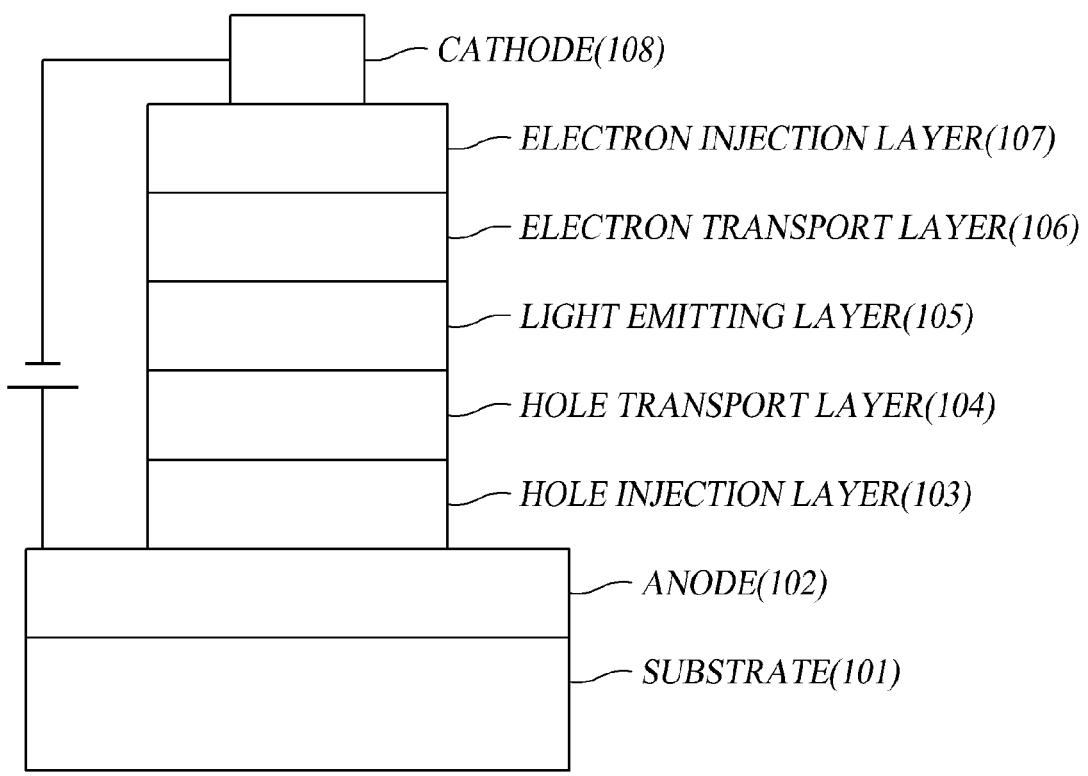
FIGS. 1 to 6 show examples of an organic light emitting device which can employ a compound according to the present invention.

Hereinafter, exemplary embodiments of the present invention will be described in detail with reference to the accompanying drawings. In reference numerals given to components of respective drawings, it should be noticed that same components are designated by the same reference numerals as far as possible although they are illustrated in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

The present invention provides a compound represented by Formula 1 below.

  Formula 1

In Formula 1, Z represents R in Formula 2 below, Y represents a group represented by Formula 2 below, n is an integer from 1 to 50, and m is an integer from 1 to 3.

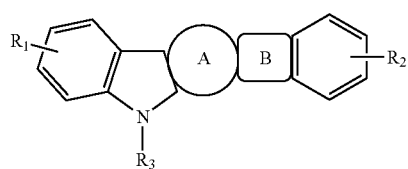  Formula 2

In Formula 2, $R_1$ through $R_3$ are the same or different, and each is independently selected from the group consisting of hydrogen, a substituted or unsubstituted aryl group having 5 to 60 nuclear carbon atoms, a substituted or unsubstituted alkyl group having 1 to 60 carbon atoms, a substituted or unsubstituted alkoxy group having 1 to 60 carbon atoms, a substituted or unsubstituted aralkyl group having 6 to 60 nuclear carbon atoms, a substituted or unsubstituted aryloxy group having 5 to 60 nuclear carbon atoms, a substituted or unsubstituted arylthio group having 5 to 50 nuclear carbon atoms, a substituted or unsubstituted alkoxycarbonyl group having 1 to 60 carbon atoms, an amino group substituted by a substituted or unsubstituted aryl group having 5 to 60 nuclear carbon atoms, a substituted or unsubstituted silyl group, a halogen atom, a cyano group, a nitro group, a hydroxyl group and a carboxyl group. $R_1$ through $R_3$ may form a ring together with an adjacent group.

$R_4$ through $R_7$ may be the same as $R_1$ through $R_3$. In Formula 2 above, a ring A may represent a heterocycle which is fused with an adjacent ring, and represented by Formula 3. Herein, X and Y are the same or different, and may represent carbon or nitrogen. Also, in Formula 2 above, a cycle B may represent a heterocycle which is fused with an adjacent ring, and represented by Formula 4. Herein, in Formula below, $R_4$ and $R_5$ may be independently the same as $R_1$ and $R_2$.

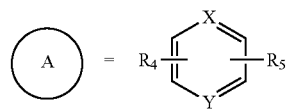  Formula 3

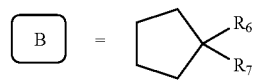  Formula 4

The present invention provides a compound represented by Formulas 5 to 7 below. In Formulas 5 to 7 below, R may be the same as $R_1$ through $R_7$ defined in Formulas 2 to 4.

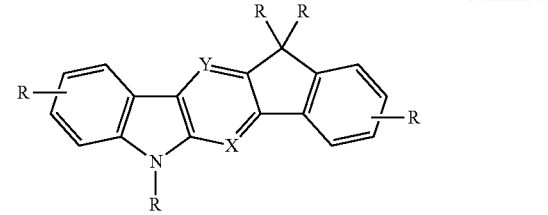  Formula 5

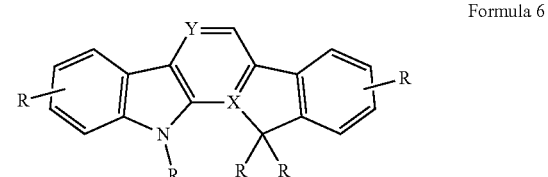  Formula 6

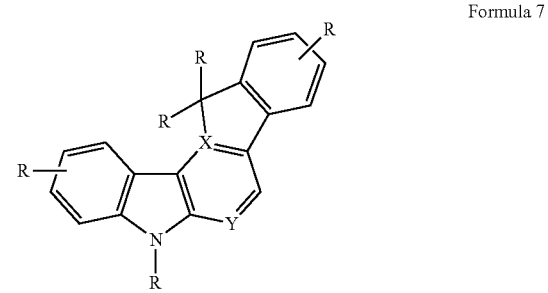  Formula 7

For the Formulas above, the specific examples of a compound having aryl or hetero aryl condensed with inden and indole are described below, but the present invention is not limited thereto.

According to one embodiment of the present invention, specific examples of a compound having aryl or hetero aryl condensed with inden and indole, represented by Formula 5, may include compounds represented by Formula 8. However, the present invention is not limited thereto.

Formula 8

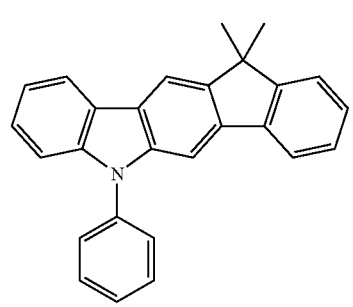

A-1

A-2
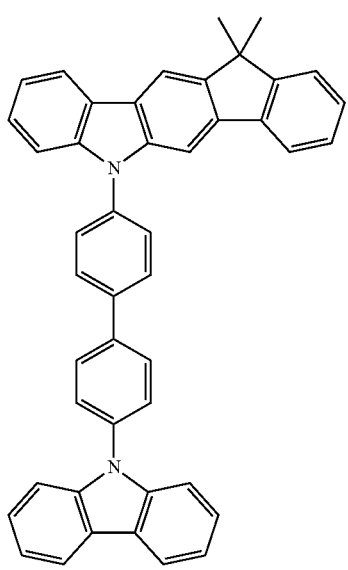
A-3
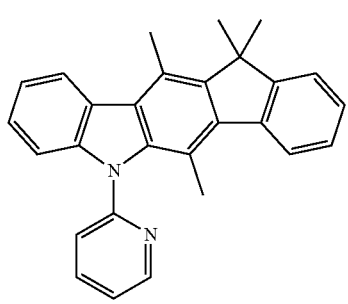
A-4
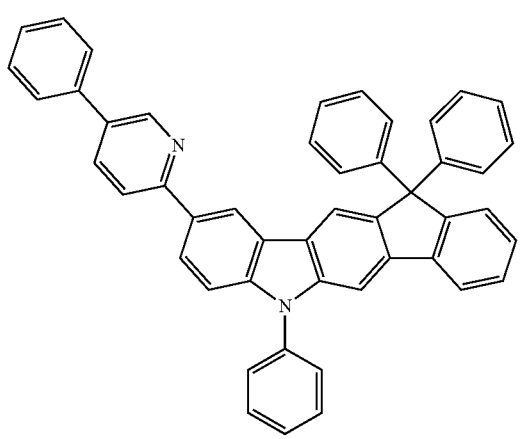
A-5
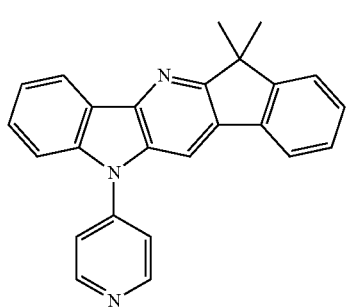
A-6
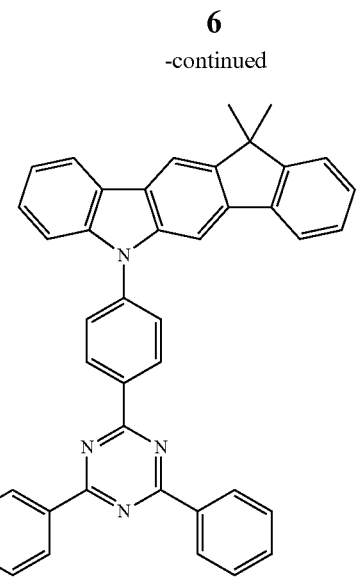
A-7
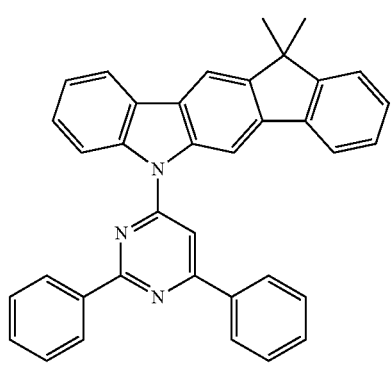
A-8
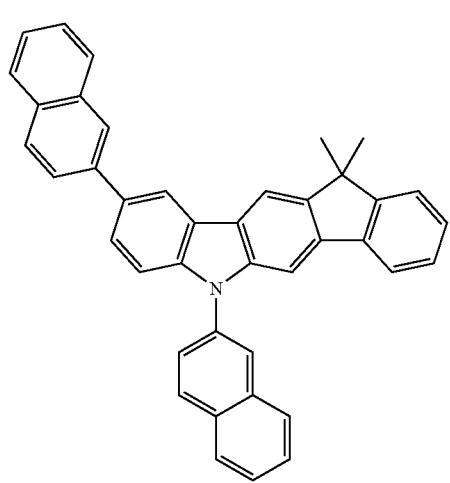

-continued
A-9
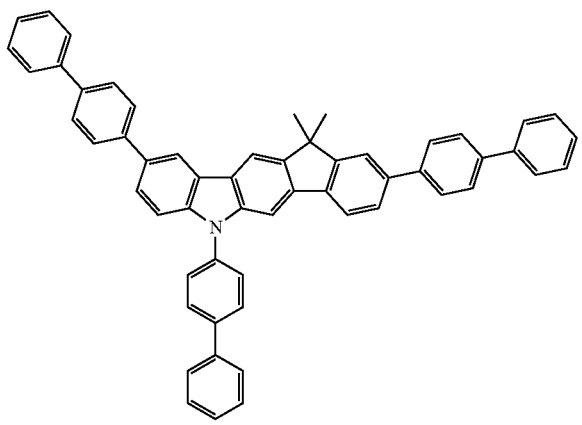
A-12
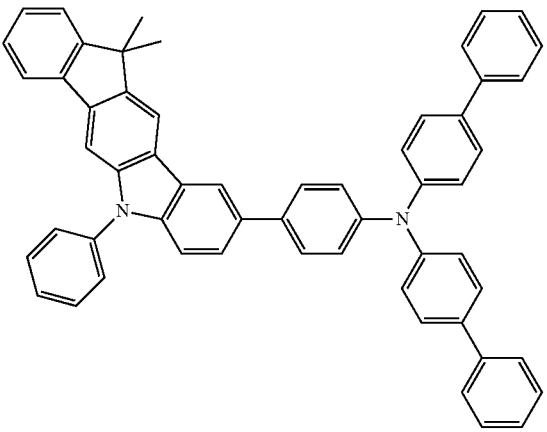
A-10
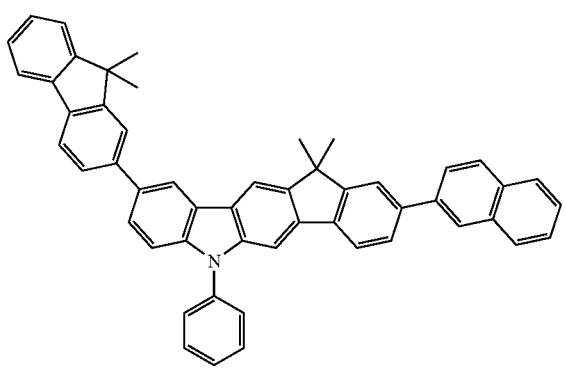
A-13
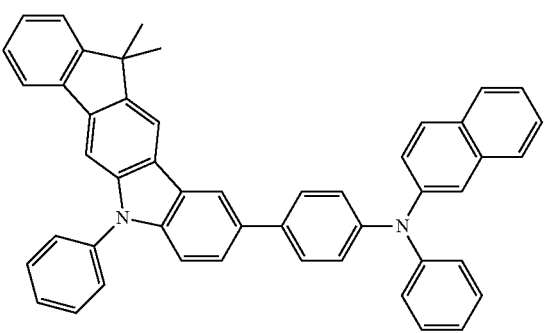
A-11
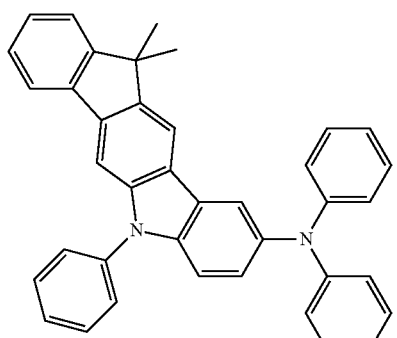
A-14
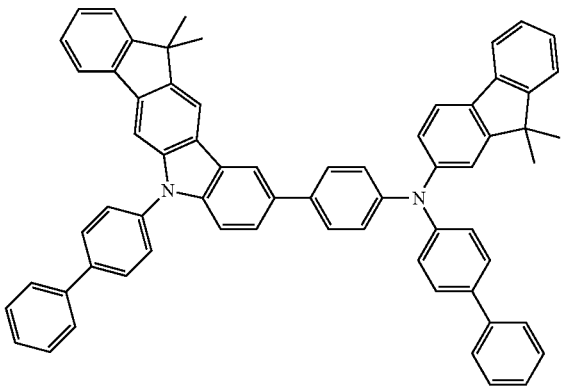
According to one embodiment of the present invention, specific examples of a compound having aryl or hetero aryl condensed with inden and indole, represented by Formula 6, may include compounds represented by Formula 9. However, the present invention is not limited thereto.
Formula 9
B-1
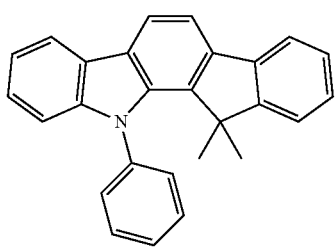

B-2
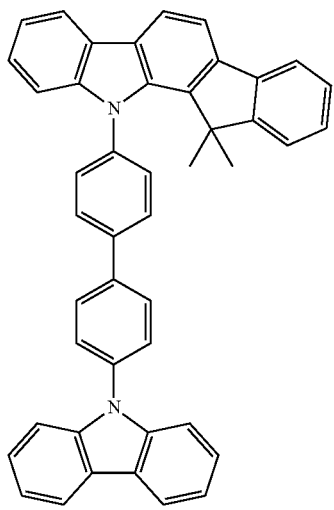
B-3
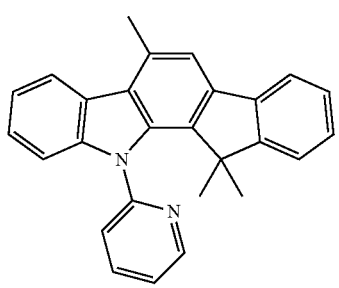
B-4
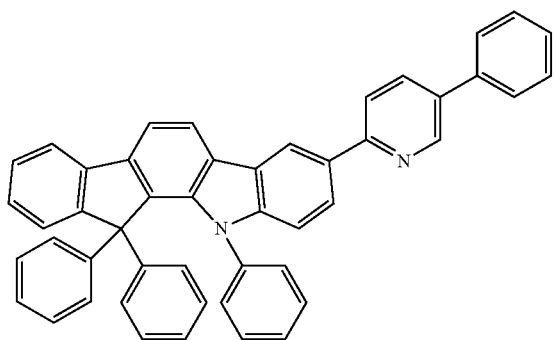
B-5
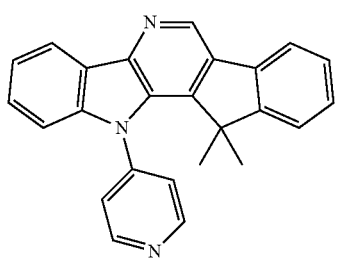

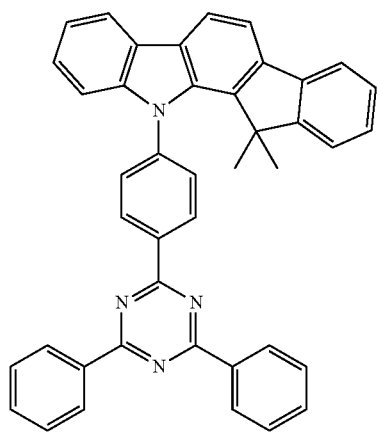
B-6
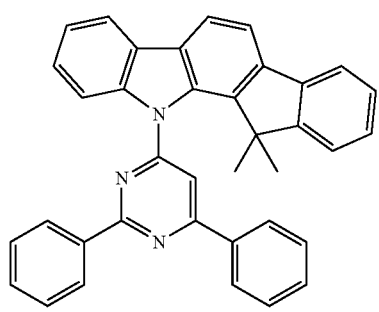
B-7
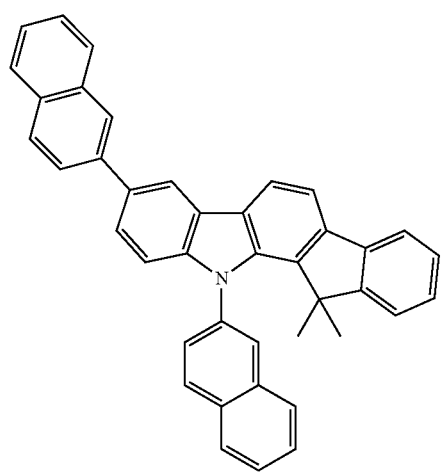
B-8

B-9
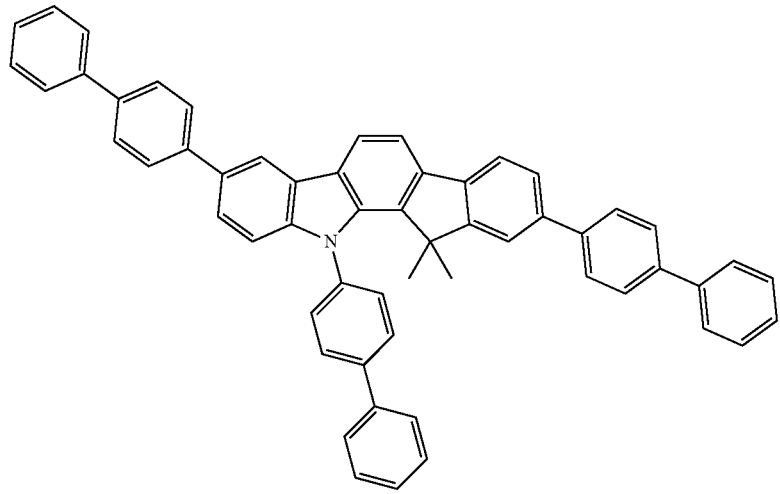
B-10
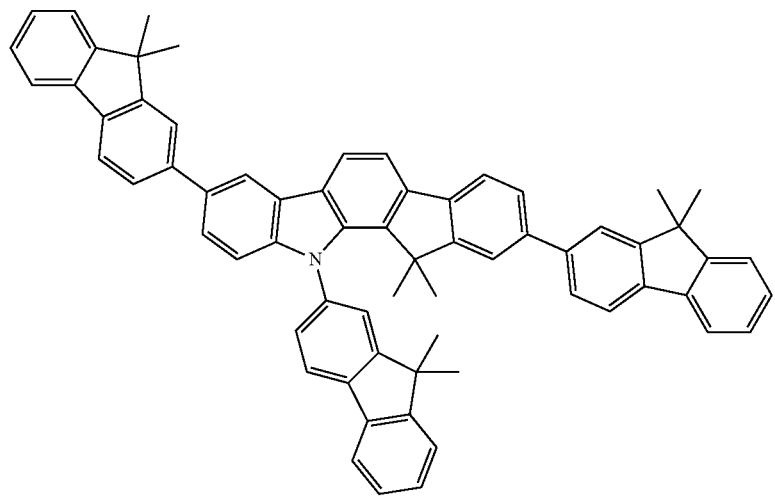
B-11
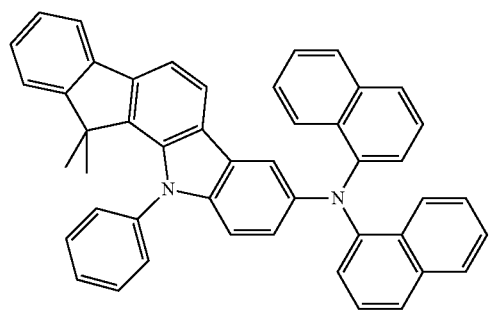

-continued
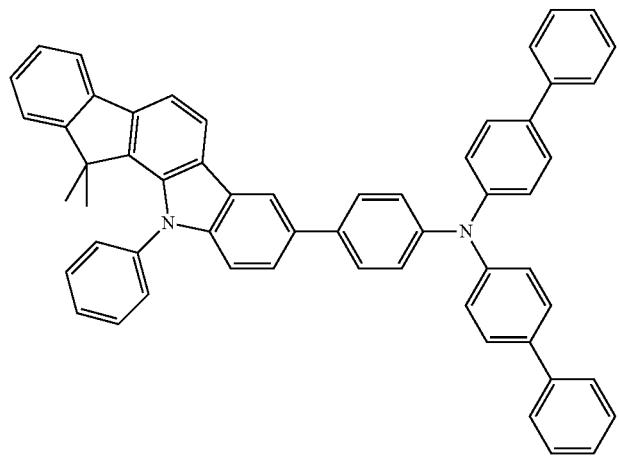
B-12
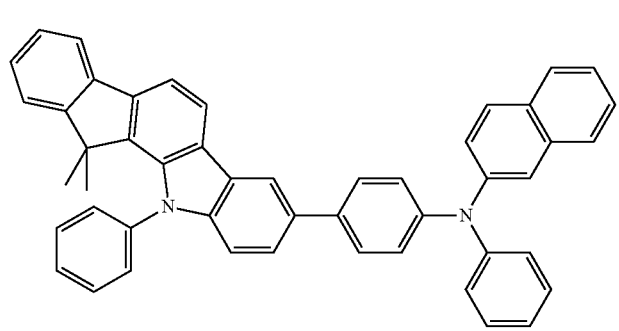
B-13
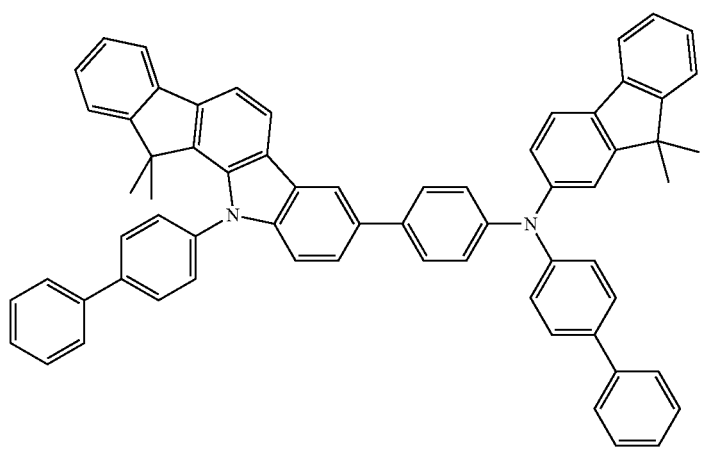
B-14

According to one embodiment of the present invention, specific examples of a compound having aryl or hetero aryl condensed with inden and indole, represented by Formula 7, may include compounds represented by Formula 10. However, the present invention is not limited thereto.
Formula 10
C-1
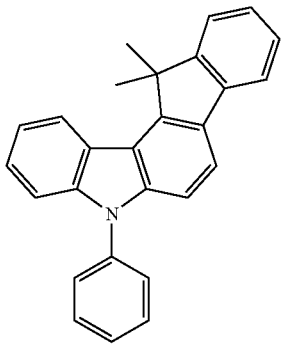
C-2
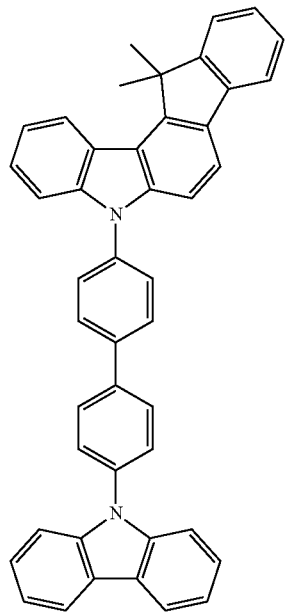
C-3
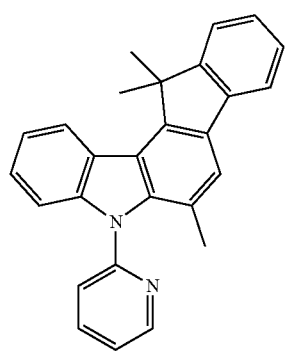
-continued
C-4
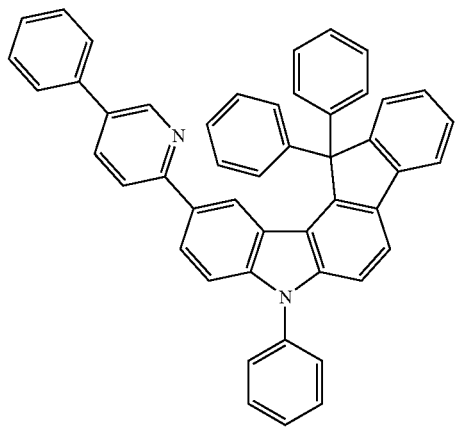
C-5
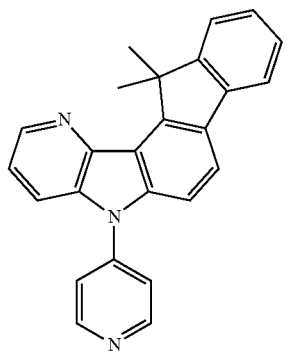
C-6
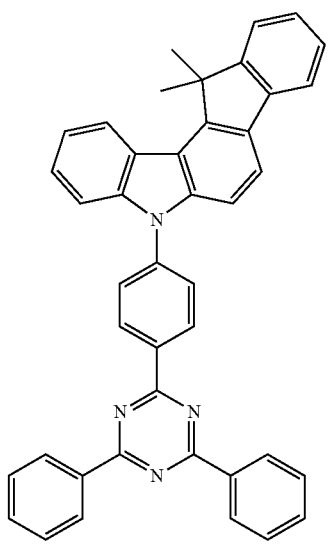

C-7
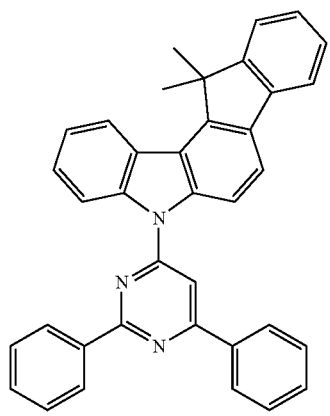
C-10
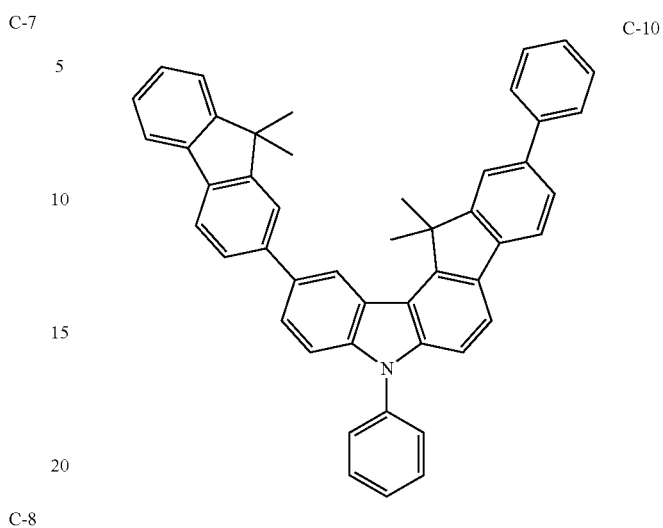
C-8
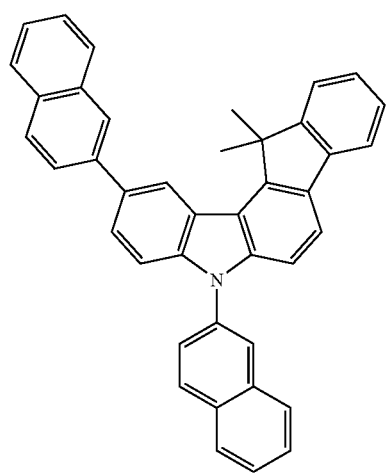
C-11
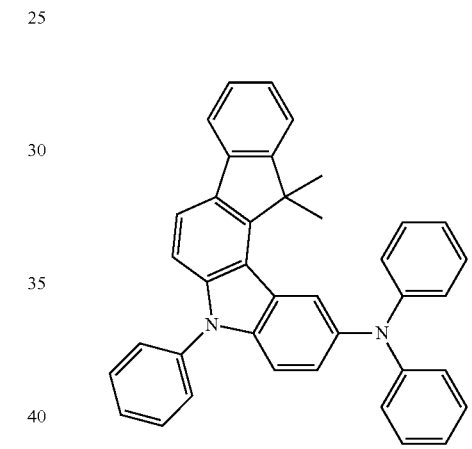
C-9
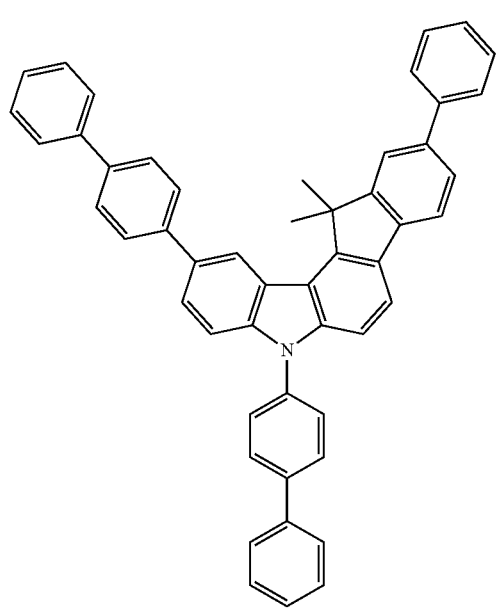
C-12
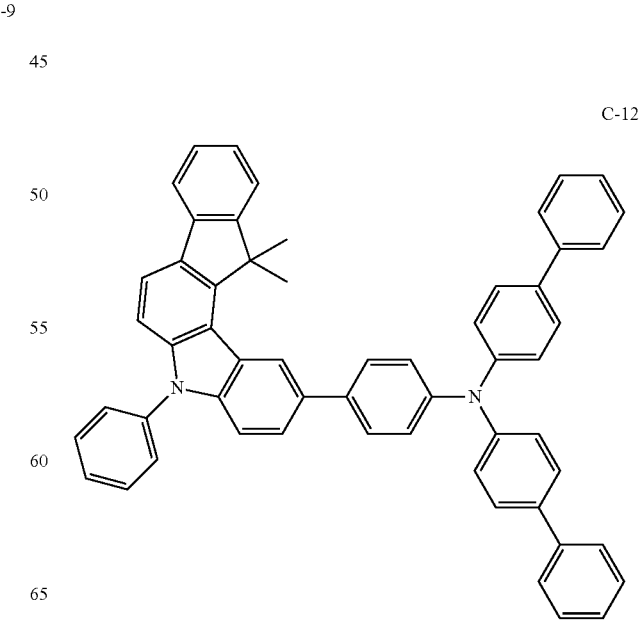

-continued

C-13

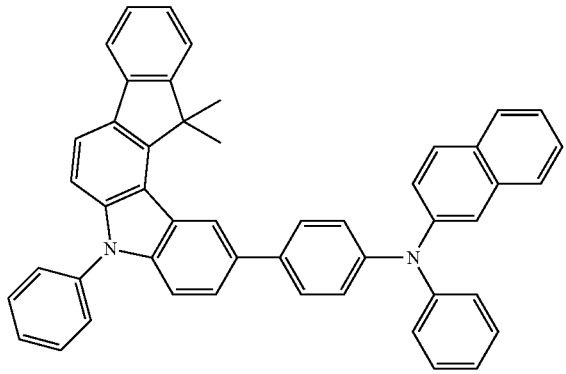

C-14

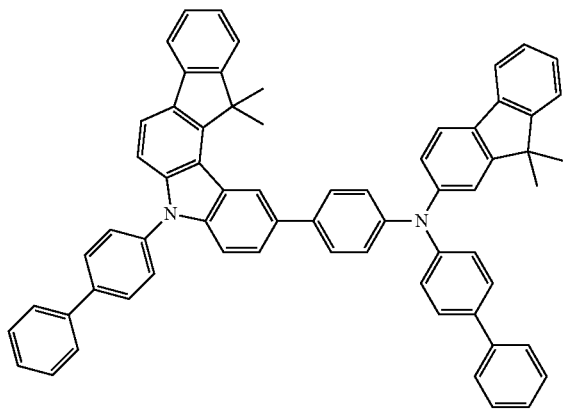

There exist various organic electronic devices which employ compounds having aryl or hetero aryl condensed with inden and indole, represented by Formulas 1 to 10, as an organic material layer. The organic electronic devices in which compounds having aryl or hetero aryl condensed with inden and indole, represented by Formulas 1 to 10, can be employed, may include, for example, an organic light emitting device (OLED), an organic solar cell, an organic photo conductor (OPC) drum, an organic transistor (organic TFT), a photodiode, an organic laser, a laser diode, and the like.

As one example of the organic light emitting devices in which compounds having aryl or hetero aryl condensed with inden and indole, represented by Formulas 1 to 10, can be used, an organic light emitting device (OLED) will be described below, but the present invention is not limited thereto. The above described compound having aryl or hetero aryl condensed with inden and indole may be applied to various organic electronic devices.

In another embodiment of the present invention, there is provided an OLED including a first electrode, a second electrode, and an organic material layer interposed between these electrodes, in which at least one of organic material layers includes the compounds represented by Formulas 1 to 10.

Figure 2:
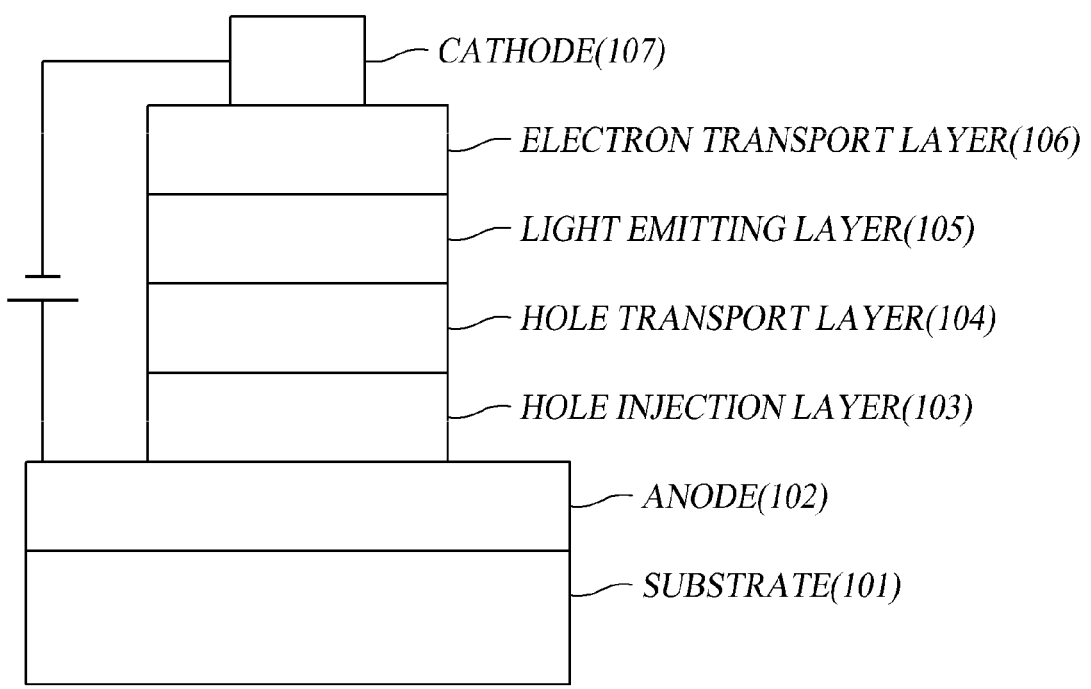
Figure 3:
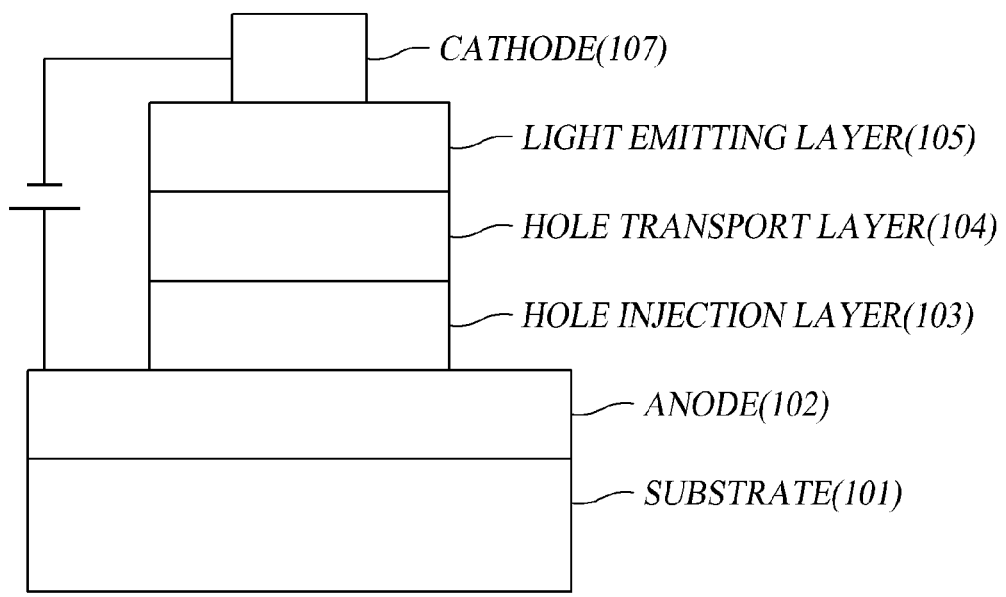
Figure 4:
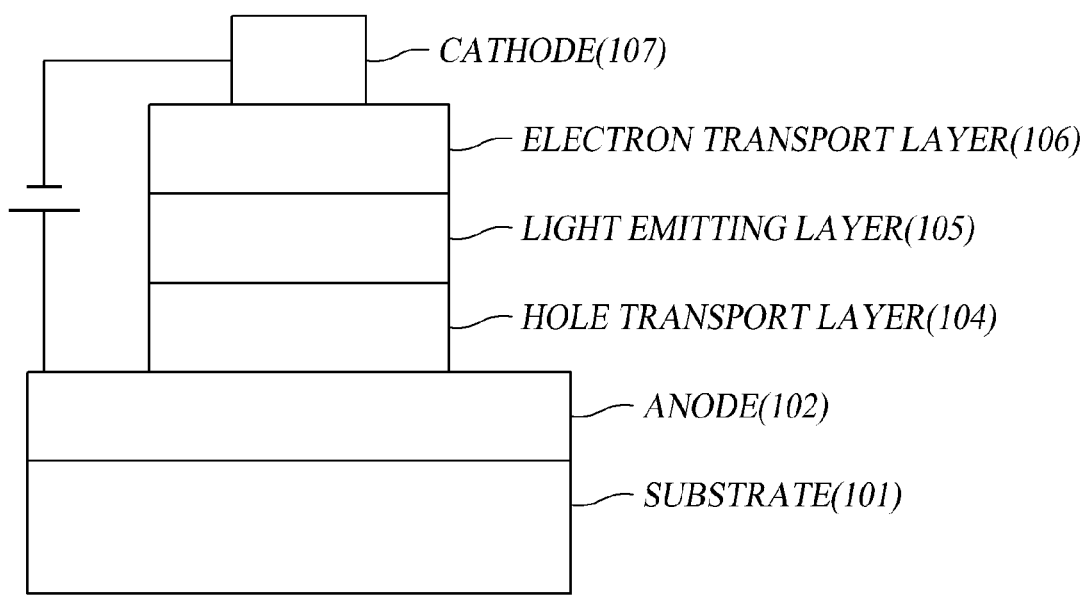
Figure 5:
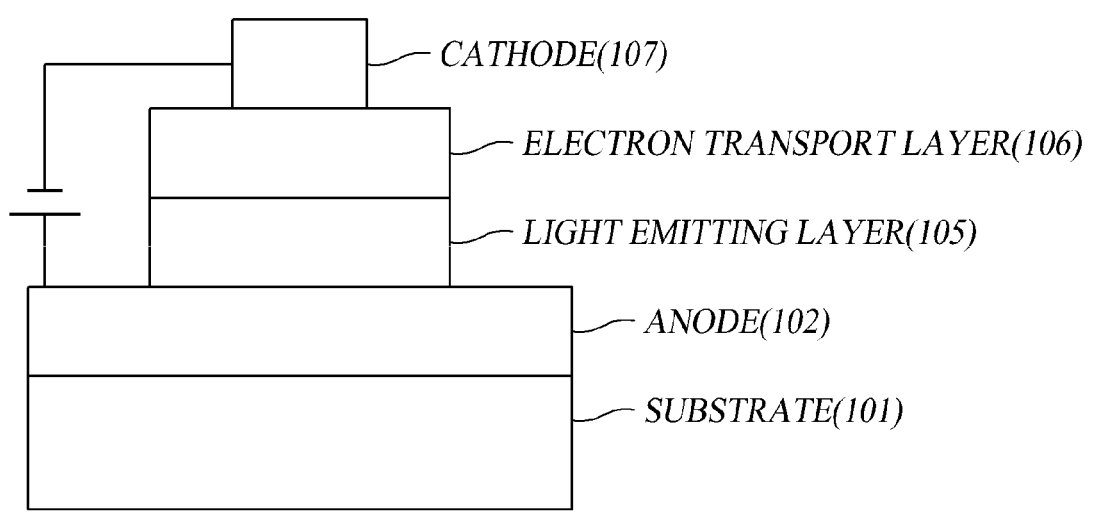
Figure 6:
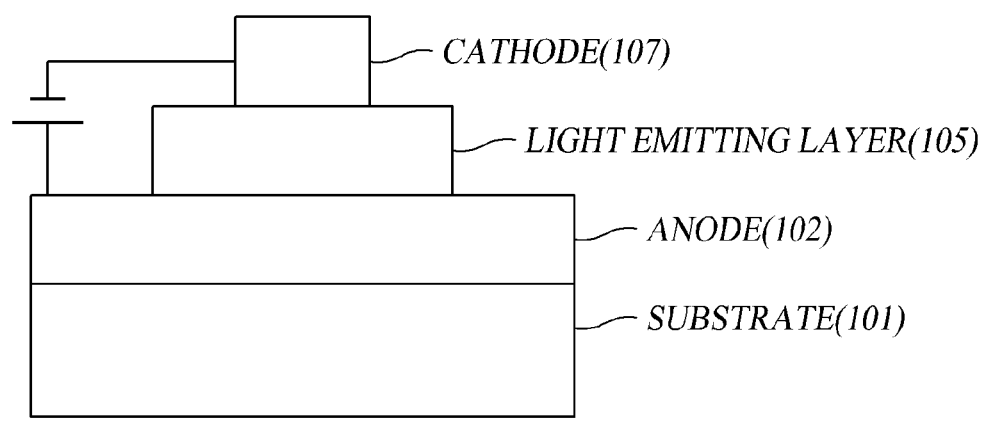

FIGS. 1 to 6 show examples of an OLED which can employ a compound according to the present invention.

The OLED according to another embodiment of the present invention may be manufactured by means of a manufacturing method and materials conventionally known in the art in such a manner that it can have a conventionally known structure, except that at least one of organic material layers including a hole injection layer, a hole transport layer, a light emitting layer, an electron transport layer, and an electron injection layer is formed in such a manner that it can include the compounds represented by Formulas 1 to 10.

The structures of the OLED according to another embodiment of the present invention are shown in FIGS. 1 to 6, but the present invention is not limited to the structures. Herein, the reference numeral 101 indicates a substrate, 102 indicates an anode, 103 indicates a hole injection layer (HIL), 104 indicates a hole transport layer (HTL), 105 indicates a light emitting layer (EML), 106 indicates an electron injection layer (EIL), 107 indicates an electron transport layer (ETL), and 108 indicates a cathode. Although not shown, such an OLED may further include a hole blocking layer (HBL) for blocking movement of holes, an electron blocking layer (EBL) for blocking movement of electrons, and a protective layer. The protective layer may be formed in such a manner that it, as an uppermost layer, can protect an organic material layer or a cathode.

Herein, a compound having aryl or hetero aryl condensed with inden and indole, represented by Formulas 1 to 10, may be included in at least one of organic material layers including a hole injection layer, a hole transport layer, a light emitting layer, and an electron transport layer. Specifically, the compound having aryl or hetero aryl condensed with inden and indole, represented by Formulas 1 to 10, may be substituted for at least one of a hole injection layer, a hole transport layer, a light emitting layer, an electron transport layer, an electron injection layer, a hole blocking layer, an electron blocking layer, and a protective layer, or may used in combination with these layers. Of course, the compound may be used for not only one layer of the organic material layers but also two or more layers.

Especially, the compound having aryl or hetero aryl condensed with inden and indole, represented by Formulas 1 to 10, may be used as a material for hole injection, hole transport, electron injection, electron transport, light emission, and passivation (capping) in an organic electronic device. Especially, it may be used alone as a light emitting material, a host or dopant in host/dopant, a hole injection layer, and a hole transport layer.

For example, in manufacturing of the OLED according to another embodiment of the present invention, a metal, a conductive metal oxide, or an alloy thereof is deposited on a substrate by means of PVD (physical vapor deposition) such as sputtering or e-beam evaporation) so as to form an anode, and then an organic material layer including a hole injection layer, a hole transport layer, a light emitting layer, an electron transport layer, and an electron injection layer is formed thereon, and a material used as a cathode is deposited thereon.

Besides, on a substrate, a cathode material, an organic material layer, and an anode material are sequentially deposited so as to provide an organic electronic device. The organic material layer may be formed in a multi-layered structure including a hole injection layer, a hole transport layer, a light emitting layer, an electron transport layer, and an electron injection layer, but the present invention is not limited thereto. It may be formed in a single layer structure. Further, the organic material layer may be manufactured with a smaller number of layers by using various polymer materials by means of a solvent process (e.g., spin coating, dip coating, doctor blading, screen printing, inkjet printing, or thermal transfer) instead of deposition.

In the OLED according to another embodiment of the present invention, the organic material layer, for example, a light emitting layer, may be formed by a soluble process of the above described compound having aryl or hetero aryl condensed with inden and indole.

The substrate is a support for the OLED, and may employ a silicon wafer, a quartz or glass plate, a metallic plate, a plastic film or sheet.

On the substrate, an anode is positioned. Such an anode allows holes to be injected into a hole injection layer positioned thereon. As an anode material, a material having a high work function is preferably used so that injection of holes into an organic material layer can be smoothly carried out. Specific examples of an anode material used for the present invention may include: metals (such as vanadium, chromium, copper, zinc, gold) or alloys thereof; metallic oxides such as zinc oxide, indium oxide, indium tin oxide (ITO), indium zinc oxide (IZO); a metal-oxide combination such as ZnO:Al or $SnO_2$:Sb; and conductive polymers such as poly(3-methylthiophene), poly[3,4-(ethylene-1,2-dioxy)thiophene](PEDT), polypyrrole and polyaniline, but the present invention is not limited thereto.

On the anode, a hole injection layer is positioned. A material for such a hole injection layer is required to have a high efficiency for injecting holes from an anode, and to be able to efficiently transport the injected holes. For this, the material has a low ionization potential, a high transparency against visible light, and a high stability for holes.

As a hole injection material, a material into which holes can be well injected from an anode at a low voltage is used. Preferably, HOMO (highest occupied molecular orbital) of the hole injection material ranges from a work function of an anode material to HOMO of adjacent organic material layers. Specific examples of the hole injection material may include metal porphyrine-, oligothiophene-, and arylamine-based organic materials, hexanitrile hexaazatriphenylen- and quinacridone-based organic materials, perylene-based organic materials, and anthraquinone-, polyaniline-, and polythiophene-based conductive polymers, but the present invention is not limited thereto.

On the hole injection layer, a hole transport layer is positioned. Such a hole transport layer receives holes transferred from the hole injection layer and transfers them to an organic luminescence layer positioned thereon. Further, the hole transport layer has a high hole mobility and a high hole stability and performs a role of blocking electrons. Besides these general requirements, it requires heat-resistance against a device when applied for car display, and thus is preferably made of a material having a glass transition temperature (Tg) of 70° C. or more. The examples of a material satisfying these conditions may include NPD (or NPB), spiro-arylamine-based compound, perylene-arylamine-based compound, azacycloheptatriene compound, bis(diphenylvinylphenyl)anthracene, silicongermaniumoxide compound, silicon-based arylamine compound, and the like.

Especially, the compound having aryl or hetero aryl condensed with inden and indole, represented by Formulas 1 to 10, may be used as a hole injection layer and a hole transport layer.

On the hole transport layer, an organic luminescence layer is positioned. Such an organic luminescence layer is made of a material having a high quantum efficiency, in which holes and electrons which are injected from an anode and a cathode, respectively, are recombined so as to emit light. As a light emitting material, a material allowing electrons and holes transferred from a hole transport layer and an electron transport layer, respectively, to be combined so as to emit visible light is used. Preferably, a material having a high quantum efficiency against fluorescence or phosphorescence is used.

As a material or a compound satisfying these conditions, for a green color, Alq3 may be used, and for a blue color, Balq(8-hydroxyquinoline beryllium salt), DPVBi(4,4'-bis(2,2-diphenylethenyl)-1,1'-biphenyl) based, Spiro material, spiro-DPVBi (Spiro-4,4'-bis(2,2-diphenylethenyl)-1,1'-biphenyl), LiPBO(2-(2-benzoxazoyl)-phenol lithium salt), bis(diphenylvinylphenylvinyl)benzene, aluminum-quinoline metal complex, imidazole, thiazol and oxazole-metal complex, or the like may be used. In order to improve the luminous efficiency of blue color, perylene, and BczVBi(3,3'-[(1,1'-biphenyl)-4,4'-diyldi-2,1-ethenediyl]bis(9-ethyl)-9H-carbazole; DSA(distrylamine)) may be doped in a small amount. For a red color, a green light emitting material is doped with DCJTB([2-(1,1-dimethylethyl)-6-[2-(2,3,6,7-tetrahydro-1,1,7,7-tetramethyl-1H,5H-benzo(ij)quinolizin-9-yl)ethenyl]-4H-pyran-4-ylidene]-propanedinitrile) in a small amount. When a process such as inkjet printing, roll coating, spin coating, is used to form a light emitting layer, polyphenylenevinylene (PPV)-based polymer or poly fluorine may be used for an organic luminescence layer.

As described above, the compound having aryl or hetero aryl condensed with inden and indole, represented by Formulas 1 to 10, may be used alone as a light emitting material in a light emitting layer, or host or dopant in host/dopant, or may form a corresponding layer in combination with conventional materials.

On the organic luminescence layer, an electron transport layer is positioned. Such an electron transport layer requires a material which has a high efficiency for electrons injected from a cathode positioned thereon, and can efficiently transport the injected electrons. For this, a material having a high electron affinity, a high electron mobility, and a high electron stability is required. The examples of an electron transport material satisfying these conditions may include Al complex of 8-hydroxyquinoline; complex including $Alq_3$; organic radical compound; and hydroxyflavone-metal complex, but the present invention is not limited thereto.

On the electron transport layer, an electron injection layer is layered. The electron injection layer may be manufactured by using a metal complex compound (such as Balq, Alq3, Be(bq)2, Zn(BTZ)2, Zn(phq)2, PBD, spiro-PBD, TPBl, and Tf-6P) or a low molecular material including an aromatic compound having an imidazole ring or a boron compound. Herein, the electron injection layer may be formed in a thickness range of 100 Å to 300 Å.

On the electron injection layer, a cathode is positioned. Such a cathode performs a role of injecting electrons into the electron injection layer. As a material for the cathode, the same material as that used for an anode may be used. In order to achieve efficient electron injection, a metal having a low work function is more preferable. Especially, metals such as tin, magnesium, indium, calcium, sodium, lithium, aluminum, silver, or alloys thereof may be used. Further, a double-layered electrode (e.g., lithiumfluoride and aluminum, lithium oxide and aluminum, and strontium oxide and aluminum) with a thickness of 100 μm or less may be used.

The OLED according to the present invention may be manufactured in a front luminescent type, a rear luminescent type, or a both-side luminescent type according to its materials.

Meanwhile, the present invention provides a terminal which includes a display device and a control part for driving the display device, the display device including the above described OLED. The terminal means a wired/wireless communication terminal which is currently used or will be used in the future. The above described terminal according to the present invention may be a mobile communication terminal such as a cellular phone, and may include all kinds of terminals such as a PDA, an electronic dictionary, a PMP, a remote control, a navigation unit, a game player, various kinds of TVs, and various kinds of computers.

EXAMPLE

Hereinafter, the present invention will be described more specifically with reference to Preparation Examples and Experimental Examples. However, the following examples are only for illustrative purposes and are not intended to limit the scope of the invention.

Preparation Example

Hereinafter, Preparation Examples or Synthesis Examples of the compounds having aryl or hetero aryl condensed with inden and indole, represented by Formulas 8 to 10, will be described. However, since there are many compounds having aryl or hetero aryl condensed with inden and indole, represented by Formulas 8 to 10, one compound or two compounds from among the compounds will be exemplified. The person skilled in the art should realize that other compounds having aryl or hetero aryl condensed with inden and indole can be prepared although they are not exemplified in Preparation Examples as described below.

Synthesis Method of Intermediate

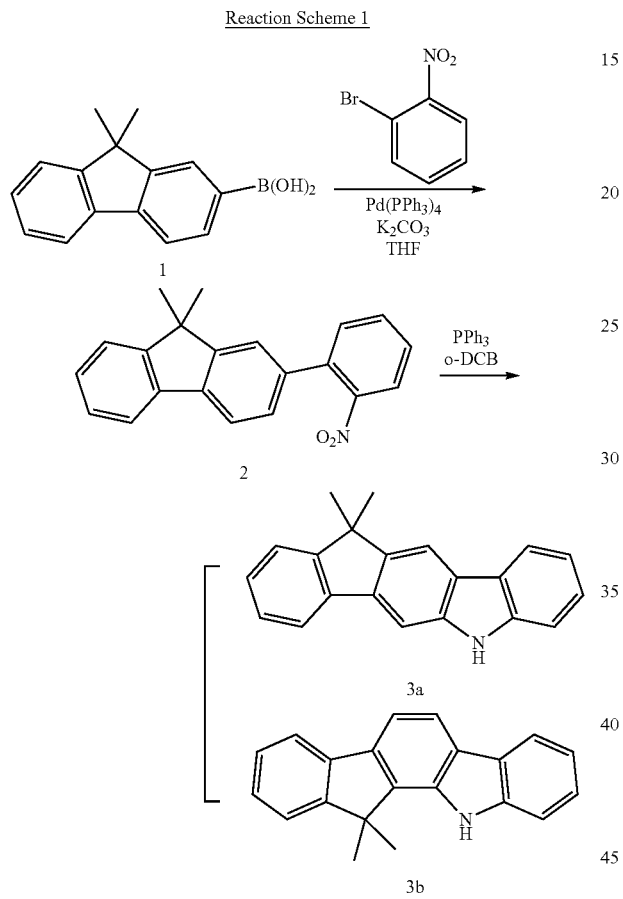

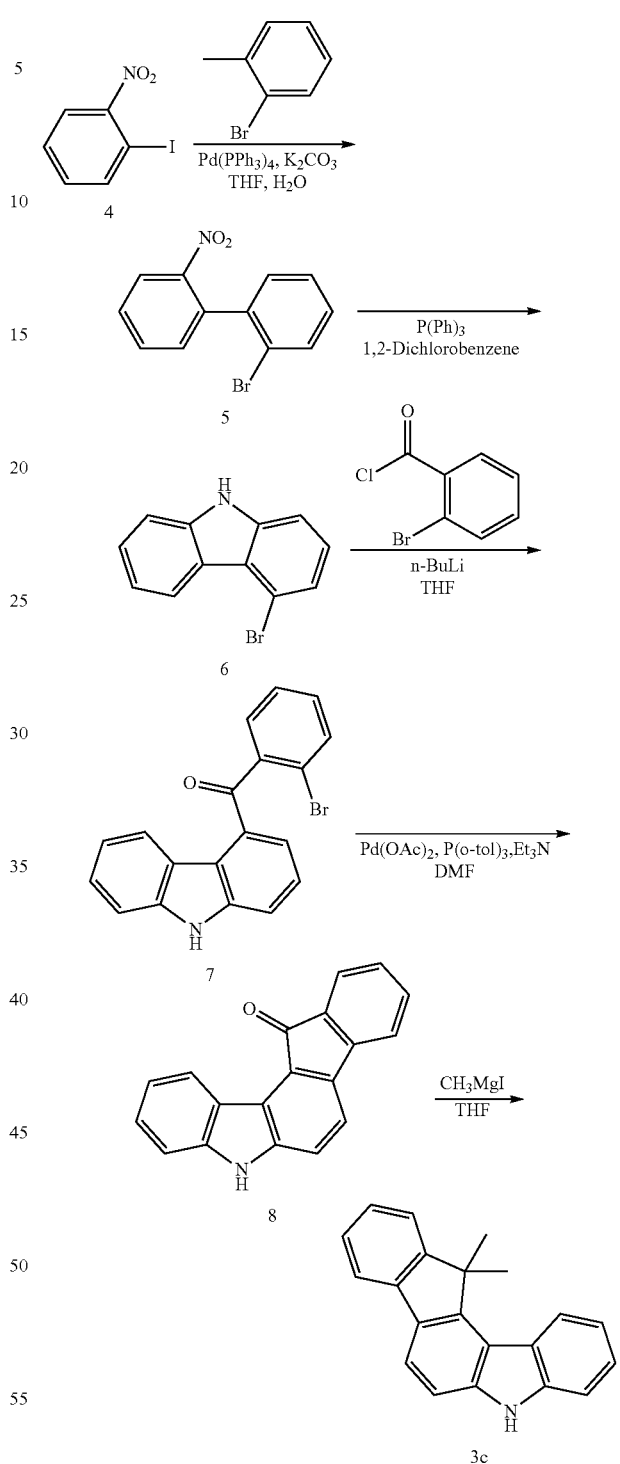

Synthesis Method of Intermediate 2

Under an argon atmosphere, 1-bromo-2-nitrobenzene (12.12 g 60 mmol), an intermediate 1 (11.90 g, 50 mmol), and tetrakis triphenyl phosphine palladium (0.5 g, 4.32 mmol) were added in THF 500 ml, and water 250 ml added with $K_2CO_3$, followed by heating and refluxing for 24 hours. The obtained solid was washed with water and methanol, and purified by silica gel column chromatography to give an intermediate 2 (yield=78%).

Synthesis Method of Intermediate 3a and 3b

A compound 2 (1.89 g, 5.98 mmol) dissolved in orthodichlorobenzene, and triphenylphosphinepalladium (3.92 g, 14.85 mmol) were added in 2-neck, followed by refluxing and stirring for 24 hours. Then, the color of solvent was changed from yellow to brown. The resultant product was concentrated by raising the temperature up to room temperature, and then purified by silica gel column chromatography to give intermediates 3a and 3b with yields of 45% and 45%, respectively.

Synthesis Method of Intermediate 5

In a 1000 mL two-necked round-bottom flask, 1-iodo-2-nitrobenzene (102.74 mmol, 25.58 g), 2-bromophenylboronic acid (102.74 mmol, 20.63 g), tetrakistriphenylphosphine palladium(0) (3.08 mmol, 3.56 g), and potassium cabonate (308.21 mmol, 42.60 g) were added, and then, as a solvent, 300 mL of Tetrahydrofuran (THF) and 100 mL of water were added thereto, followed by stirring at 80° C. The temperature of the reaction solution was lowered to a room temperature, and dichloromethane was used for extraction. The obtained extract was dried with magnesium sulfate anhydrous and concentrated. The resultant mixture was purified by silica gel column chromatography to give 20.00 g of a white solid title compound with a yield of 70%.

Synthesis Method of Intermediate 6

A compound 5 dissolved in orthodichlorobenzene, and triphenylphosphinepalladium were added in 2-neck, followed by refluxing and stirring for 24 hours. Then, the color of solvent was changed from yellow to brown. The resultant product was concentrated by raising the temperature up to room temperature, and then purified by silica gel column chromatography to give an intermediate 6 with a yield of 75%.

Synthesis Method of Intermediate 7

In a 500 mL two-necked round-bottom flask, 4-bromo-9H-carbazole (67.19 mmol, 16.53 g) was added, and nitrogen was filled. Then, 300 mL of anhydrous Tetrahydrofuran (THF) was added thereto for dissolution, and then at −78° C., n-Butyllithium in Hexane 2.5M (70.55 mmol, 28.22 mL) was slowly added thereto. The temperature was adjusted to room temperature, 30-min stirring was carried out, then the temperature was adjusted to −78° C., and 2-bromobenzoyl chloride (67.19 mmol, 14.74 g) dissolved anhydrous Tetrahydrofuran (THF) was slowly added. The temperature was adjusted to room temperature, and stirring was carried out. After the completion of the reaction, dichloromethane was used for extraction. The obtained extract was dried with magnesium sulfate anhydrous and concentrated. The resultant mixture was purified by silica gel column chromatography to give 18.02 g of a yellow solid intermediate 7 with a yield of 77%.

Synthesis Method of Intermediate 8

In a 1000 mL two-necked round-bottom flask, (2-bromophenyl)(9H-carbazol-4-yl)methanone (85.66 mmol, 27.77 g), and Pd(OAc)$_2$ (0.86 mmol, 0.19 g) were added, and nitrogen was filled. Then, as a solvent, 500 mL of Dimethylformamide was added thereto, and P(o-tol)$_3$ (1.71 mmol, 0.52 g) was added thereto, followed by stirring at 90° C. After the completion of the reaction, the temperature of the reaction solution was lowered to a room temperature, and ethanol was added thereto so as to filter the precipitate. The resultant mixture was purified by silica gel column chromatography (eluent-dichloromethane:n-hexane=3:7) to give 15.0 g of a white solid title compound with a yield of 50%.

Synthesis Method of Intermediate 3c

In a 500 mL two-necked round-bottom flask, an intermediate 8 was added, and nitrogen was filled. Then, 300 mL of anhydrous THF was added thereto for dissolution, and then at −78° C., Methylmagnesium bromide 3M (63.03 mmol, 25.32 mL) was slowly added thereto. The temperature was slowly adjusted to room temperature, and stirring was carried out. After the completion of the reaction, dichloromethane was used for extraction. The obtained extract was dried with magnesium sulfate anhydrous and concentrated. The resultant mixture was purified by silica gel column chromatography to give a yellow solid title intermediate 3c with a yield of 80%.

Synthesis Method of Compound A-9

Reaction Scheme 3

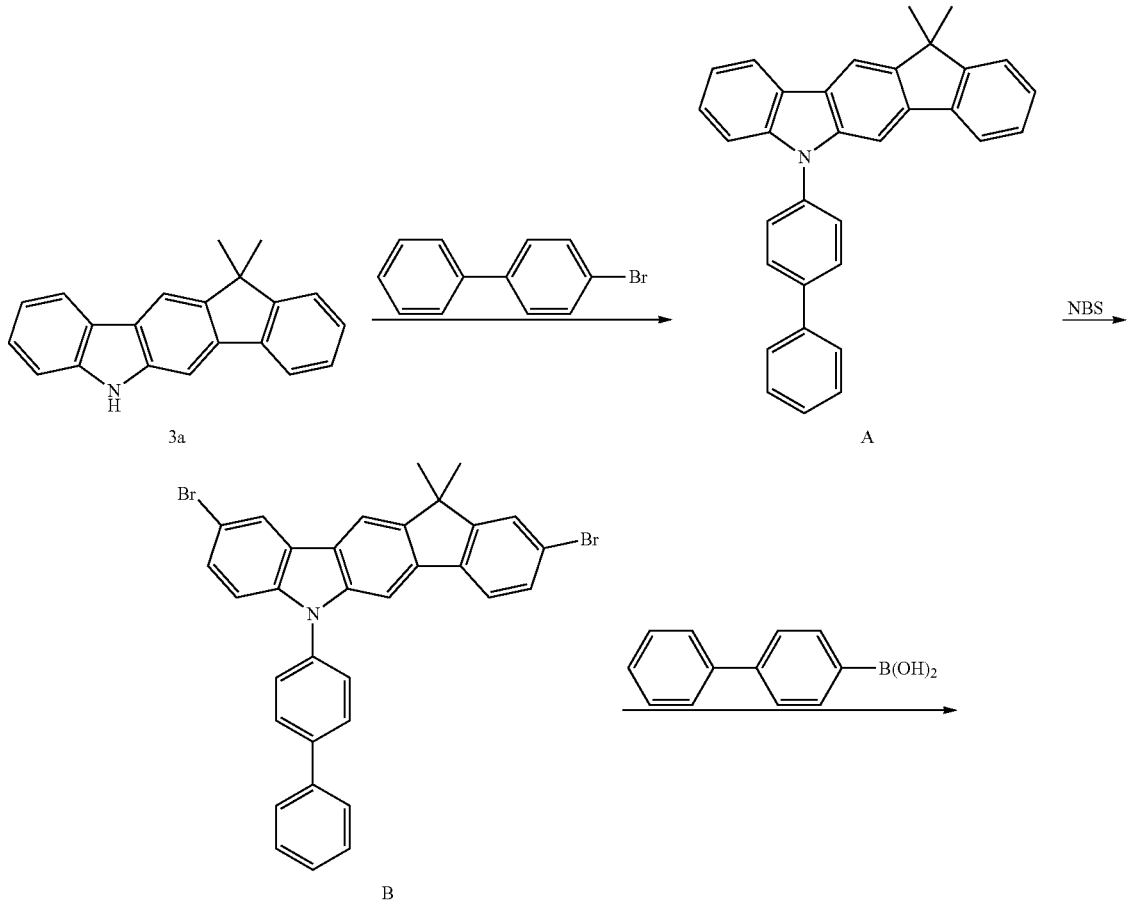

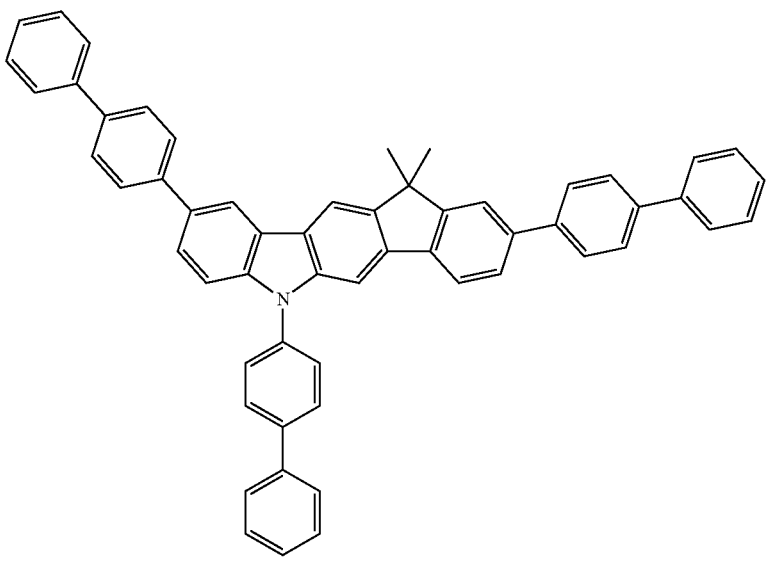

A-9

Synthesis of Intermediate A

In a 250 mL two-necked flask, a compound 3a 0.48 g (1.70 mmol), and 4-bromobiphenyl 0.40 g (1.70 mmol) were added, and $Pd_2(dba)_3$ 0.078 g (0.085 mmol), $(t-Bu)_3P$ 0.34 g (1.70 mmol), t-BuONa 0.36 g (3.70 mmol), and toluene 150 mL were added thereto, followed by refluxing and stirring.

The resultant product was extracted with water and MC, dried with $MgSO_4$, purified by silica gel column chromatography (MC/Hexane (3:7)), recrystallized with hexane and filtered to give an intermediate A.

Synthesis of Intermediate B

In a two-necked flask, a compound A (2 g, 4.59 mmol) was dissolved in MC. At 0° C., NBS (1.65 g, 9.20 mmol) was added thereto. After 30 minutes, the temperature was raised up to a room temperature, and 6-hour stirring was carried out.

After the completion of the reaction, the resultant product was extracted with an aqueous solution having sodium bicarbonate dissolved therein, and MC, and then extracted with water several times, and concentrated. Then, the resultant product was dried with $MgSO_4$ and filtered. The filtrate was concentrated, washed with acetone/hexane (1:3) solution, and dried to give an intermediate B.

Synthesis of Compound A-9

A compound was synthesized in the same manner as described in all synthesis processes except that an intermediate B, instead of 1-bromo-2-nitrobenzene, and biphenyl-4-yl boronic acid, instead of an intermediate 1, were used.

Synthesis of Compound B-10

Reaction Scheme 4

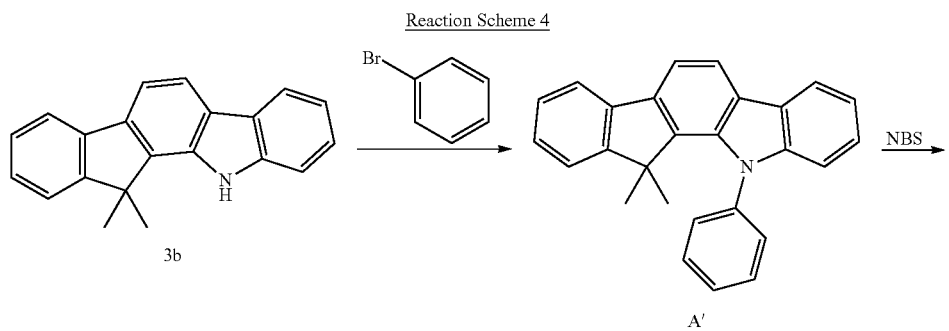

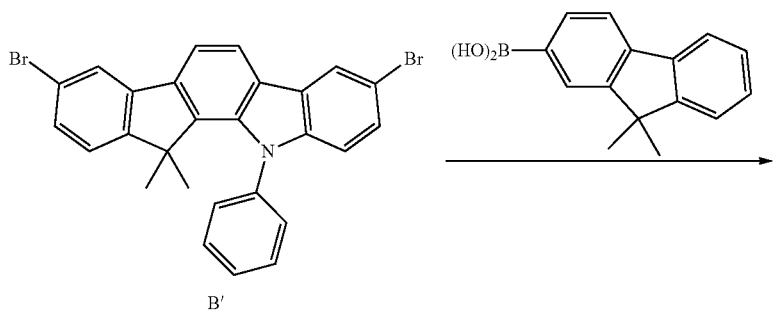

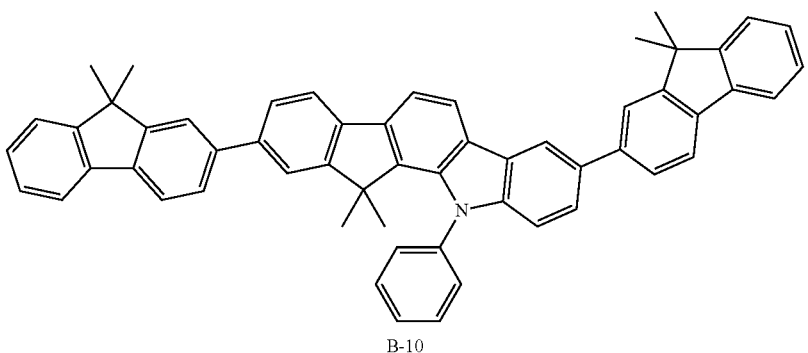

Synthesis of intermediate A'

A compound was synthesized in the same manner as described in all synthesis processes except that a compound 3b, instead of a compound 3a, and bromobiphenyl, instead of 4-bromobiphenyl, were used.

Synthesis of Intermediate B'

A compound was synthesized in the same manner as described in all synthesis processes except that a compound A', instead of a compound A was used.

Synthesis of Compound B-10

A compound was synthesized in the same manner as described in all synthesis processes except that an intermediate B', instead of 1-bromo-2-nitrobenzene, and 9,9-dimethyl-9H-fluorene-2-yl boronic acid, instead of an intermediate 1, were used.

Synthesis Method of Compound C-6

Reaction Scheme 5

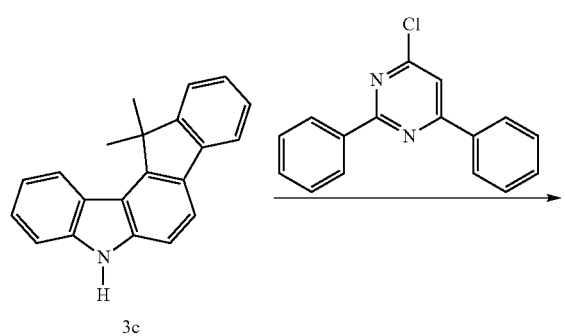

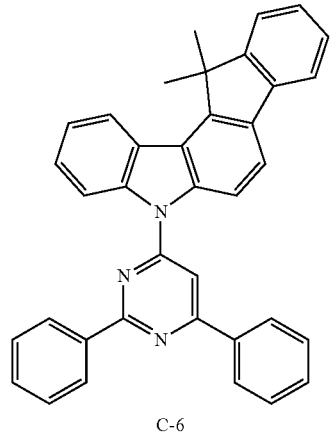

Synthesis of Compound C-6

A compound was synthesized in the same manner as described in all synthesis processes except that a compound 3c, instead of a compound 3b, and 4-chloro-2,6-diphenylpyrimidine, instead of bromobiphenyl, were used in the synthesis method of an intermediate A'.

Synthesis Method of Compound A-14

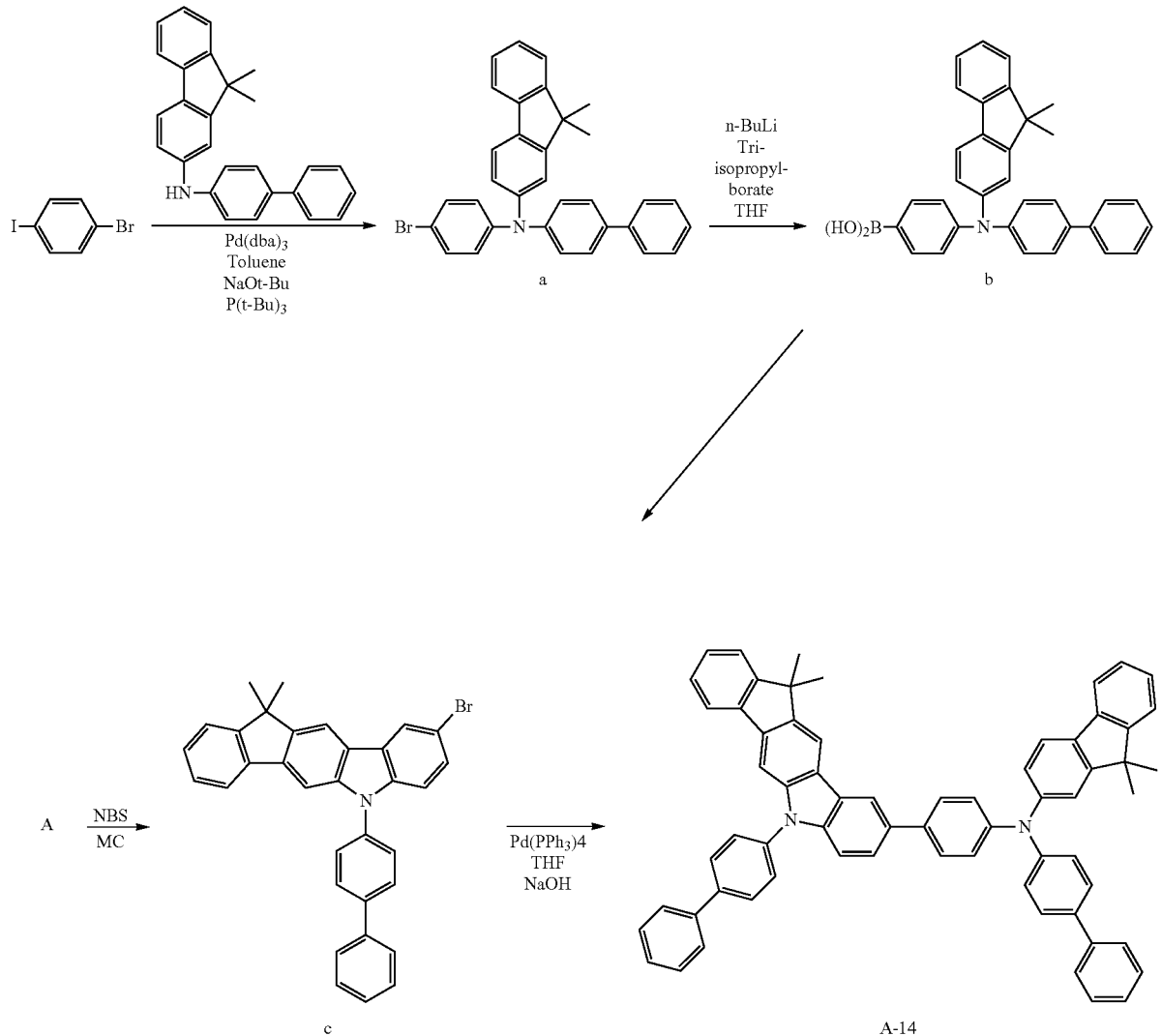

Reaction Scheme 6

Synthesis Method of Intermediate A

N-(biphenyl-4-yl)-9,9-dimethyl-9H-fluoren-2-amine, 1-Bromo-4-iodobenzene, Pd$_2$(dba)$_3$, Triphenylphosphine, and Sodium tert-butoxide were added in toluene solvent, followed by refluxing and stirring at 130° C. for 24 hours. After the completion of the reaction, the resultant product was extracted with MC and water, dried with MgSO$_4$, and concentrated. The resultant compound was purified by column chromatography to give a required compound (intermediate a) with a yield of 68%.

Synthesis Method of Intermediate B

An intermediate a was dissolved in THF, and at −78° C., n-BuLi was gradually dropped, followed by stirring for about 1 hour. Then, at −78° C., Triisopropylborate was gradually dropped, followed by stirring. Then, the resultant product was subjected to acid treatment through 1N HCl, extracted with water and EA, dried with MgSO$_4$, and recrystallized with hexane to give an intermediate b with a yield of 54%.

Synthesis Method of Intermediate C

In a two-necked flask, a compound A was dissolved in MC. At 0° C., NBS was added thereto. After 30 min, the temperature was raised up to a room temperature, and 6-hour stirring was carried out. After the completion of the reaction, the resultant product was extracted with an aqueous solution having sodium bicarbonate dissolved therein, and MC, and then extracted with water several times, and concentrated. Then, the resultant product was dried with MgSO$_4$ and filtered. The filtrate was concentrated, washed with acetone/hexane (1:3) solution, and dried to give an intermediate c.

Synthesis Method of Compound A-14

An intermediate b, an intermediate c, and Pd(PPh$_3$)$_4$ were added in THF 500 ml, and water 250 ml added with K$_2$CO$_3$, followed by heating and refluxing for 24 hours. The obtained solid was washed with water and methanol, and purified by silica gel column chromatography to give a white solid product B-20 (yield=71%).

Synthesis Method of Compound B-12

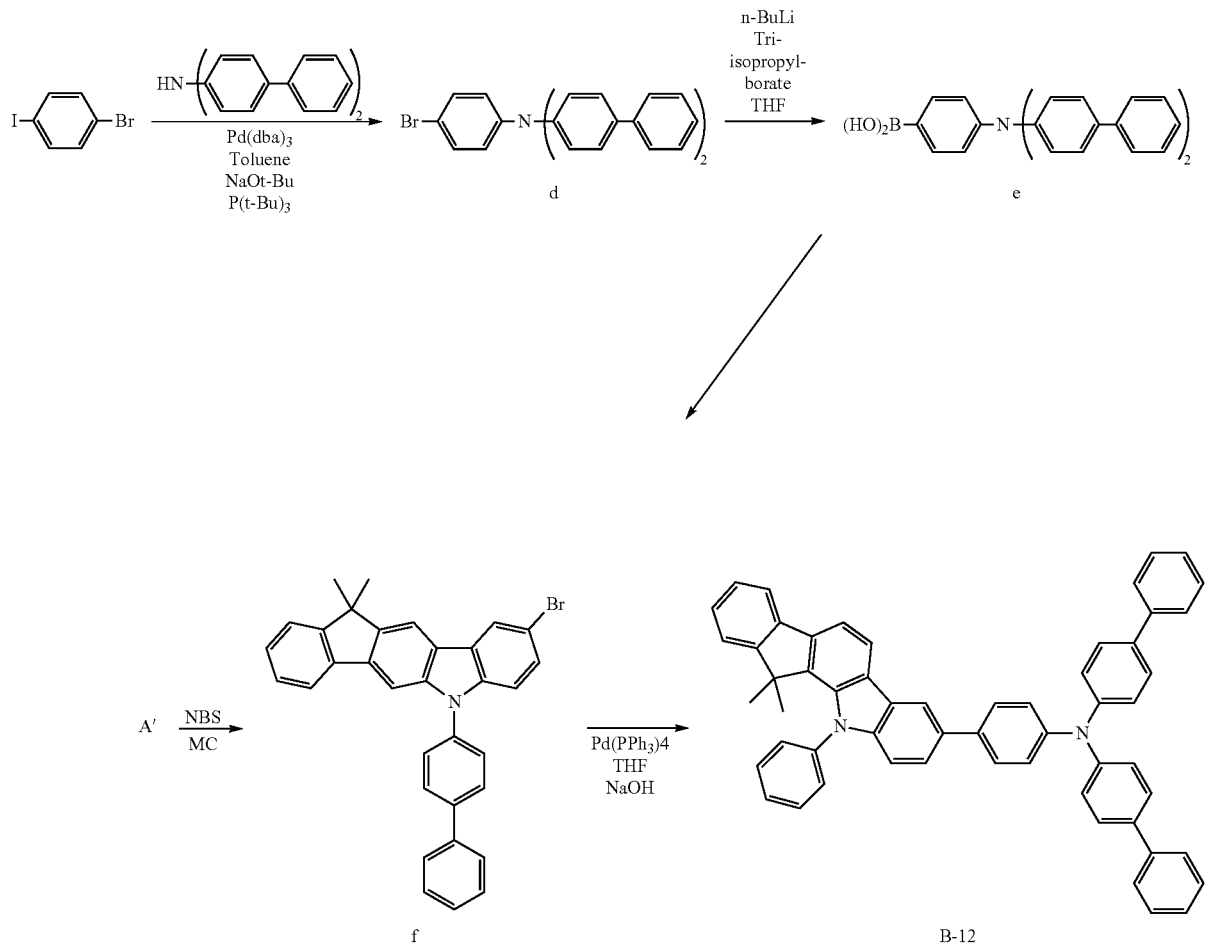

Synthesis Method of Intermediate D

The same synthesis method as that of intermediate a was carried out except that Dibiphenyl-4-ylamine, instead of N-(biphenyl-4-yl)-9,9-dimethyl-9H-fluoren-2-amine, was used in the synthesis method of an intermediate a.

Synthesis Method of Intermediate E

The same synthesis method as that of intermediate b was carried out except that an intermediate e, instead of an intermediate a, was used in the synthesis method of an intermediate b.

Synthesis Method of Intermediate F

The same synthesis method as that of intermediate c was carried out except that a compound A', instead of a compound A, was used in the synthesis method of an intermediate c.

Synthesis Method of Compound B-12

The same synthesis method as that of compound A-14 was carried out except that an intermediate f, instead of an intermediate c, and an intermediate e, instead of an intermediate b, were used in the synthesis method of an intermediate A-14.

Synthesis Method of Compound C-13

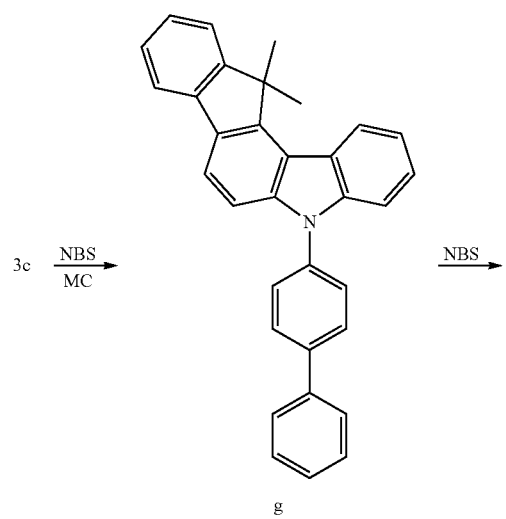

-continued

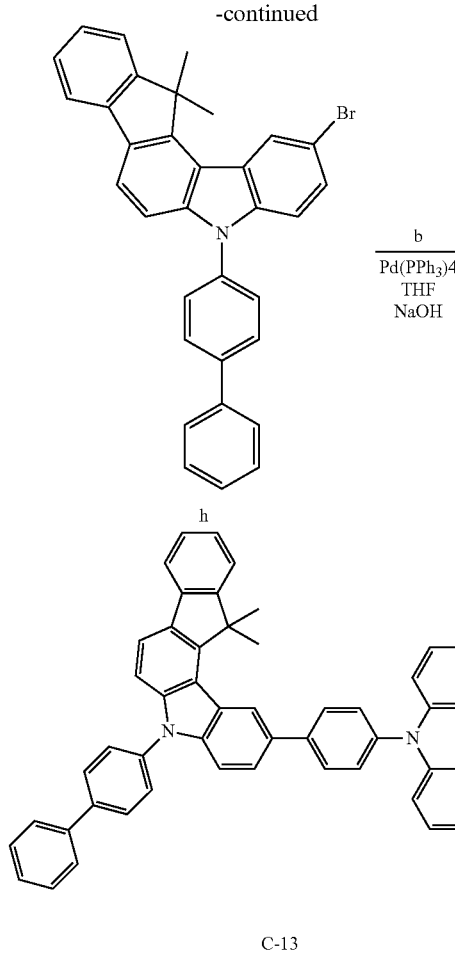

C-13

Synthesis Method of Intermediate G

The same synthesis method as that of intermediate A was carried out except that 3c, instead of 3a, was used in the synthesis method of an intermediate A.

Synthesis Method of Intermediate H

The same synthesis method as that of intermediate c was carried out except that an intermediate g, instead of an intermediate A was used in the synthesis method of an intermediate c.

Synthesis Method of Compound C-14

The same synthesis method as that of compound A-14 was carried out except that an intermediate h, instead of an intermediate c was used in the synthesis method of an intermediate A-14.

OLED Fabrication Test 1

An OLED was manufactured according to a conventional method by using each of compounds A-9, B-10, and C-6 obtained by synthesis as a light emitting host material for a light emitting layer.

First, on an ITO layer (anode) formed on a glass substrate, a copper phthalocyanine (CuPc) film as a hole injection layer was vacuum-deposited with a thickness of 10 nm.

Then, on this film, 4,4-bis[N-(1-naphthyl)-N-phenylamino]biphenyl (a-NPD) as a hole transport compound was vacuum-deposited with a thickness of 30 nm so as to form a hole transport layer. After the hole transport layer was formed, a compound 2, 3, or 4 as a phosphorescence host material was deposited on the hole transport layer so as to form a light emitting layer. At the same time, as a phosphorescent Ir metal complex dopant, tris(2-phenylpyridine)iridium (Ir(ppy)$_3$) was added. Herein, in the light emitting layer, the concentration of Ir(ppy)$_3$ was 5 wt %.

As a hole blocking layer, (1,1'-bisphenyl)-4-oleate)bis(2-methyl-8-quinolineoleate)aluminum (BAlq) was vacuum-deposited with a thickness of 10 nm, and then as an electron injection layer, tris(8-quinolinol)aluminum (Alq$_3$) was film-formed with a thickness of 40 nm. Then, LiF (alkali-metal halide) was deposited with a thickness of 0.2 nm, and Al was deposited with a thickness of 150 nm. The Al/LiF was used as a cathode while the OLED was fabricated.

Comparison Example 1

For comparison, instead of the inventive compound, a compound (CBP) represented by Formula 11 below was used as a light emitting host material so as to fabricate an OLED with the same structure as that of Test Example.

Formula 11

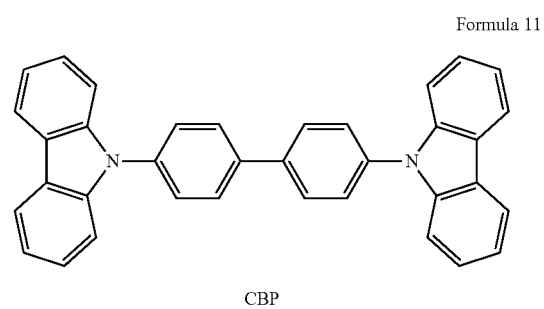 [SMILES: c1ccc2c(c1)c1ccccc1n2-c1ccc(-c2ccc(-n3c4ccccc4c4ccccc43)cc2)cc1 ; "CBP"]

CBP

TABLE 1

| | Host material of light emitting layer | Voltage (V) | current density (mA/cm$^2$) | luminous efficiency (cd/A) | chromaticity coordinates (x, y) |
|---|---|---|---|---|---|
| Example 1 | compound A-9 | 5.6 | 0.33 | 49.3 | (0.31, 0.60) |
| Example 2 | compound B-10 | 5.5 | 0.32 | 48.3 | (0.31, 0.60) |
| Example 3 | compound C-6 | 5.3 | 0.36 | 52.2 | (0.30, 0.61) |
| Comparative Example 1 | CBP | 6.1 | 0.31 | 32.6 | (0.33, 0.61) |

From the results noted in Table 1, in an OLED using the inventive material for the OLED, it is possible to obtain long-life green light with a high efficiency, and an improved color purity. Thus, the inventive material as a green phosphorescence host material for an OLED can significantly improve the luminous efficiency and lifetime.

OLED Fabrication Test 1

An OLED was manufactured according to a conventional method by using each of compounds A-14, B-12, and C-13 obtained by synthesis as a hole transport layer.

First, on an ITO layer (anode) formed on a glass substrate, a 4,4',4"-tris(N-(2-naphthyl)-N-phenylamino)-triphenylamine (2T-NATA) film as a hole injection layer was vacuum-deposited with a thickness of 10 nm.

Then, on this film, the obtained material as a hole transport compound was vacuum-deposited with a thickness of 30 nm so as to form a hole transport layer. After the formation of the hole transport layer, when the developed material was measured as a hole transport layer, a light emitting layer doped with 7% BD-052X (Idemitus, thickness of 45 nm) (BD-052X=blue fluorescent dopant, a light emitting host material=9,10-di(naphthalene-2-anthracene (AND)) was applied to the top of the hole transport layer.

As a hole blocking layer, (1,1'-bisphenyl)-4-oleate)bis(2-methyl-8-quinolineoleate)aluminum (BAlq) was vacuum-deposited with a thickness of 10 nm, and then as an electron injection layer, tris(8-quinolinol)aluminum ($Alq_3$) was film-formed with a thickness of 40 nm. Then, LiF (alkali-metal halide) was deposited with a thickness of 0.2 nm, and Al was deposited with a thickness of 150 nm. The Al/LiF was used as a cathode while the OLED was fabricated.

Comparison Example 2

When the inventive compounds were measured as a hole transport layer, for comparison, instead of the inventive compound, a compound (NPB) represented by Formula below was used as a hole transport material so as to fabricate an OLED with the same structure as that of Test Example.

Formula 12

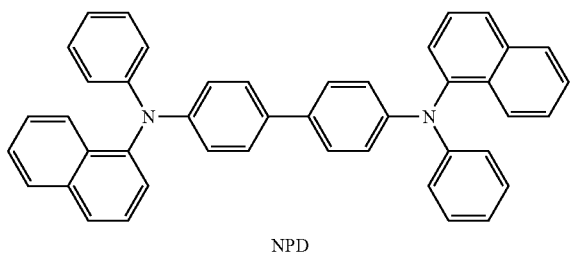

NPD

TABLE 2

| | Hole transport material | Voltage (V) | current density (mA/cm$^2$) | luminous efficiency (cd/A) | chromaticity coordinates (x, y) |
| --- | --- | --- | --- | --- | --- |
| Example 1 | compound A-14 | 5.8 | 12.72 | 9.8 | (0.15, 0.14) |
| Example 2 | compound A-12 | 5.8 | 12.92 | 9.6 | (0.15, 0.13) |
| Example 3 | compound B-13 | 5.9 | 12.77 | 9.2 | (0.15, 0.14) |
| Comparative Example 1 | NPB | 7.2 | 13.35 | 7.5 | (0.15, 0.15) |

From the results noted in Table 2, in an OLED using the inventive material for the OLED, it is possible to obtain blue light with a high efficiency, and an improved color purity. Thus, the inventive material as a hole transport material for an OLED can significantly improve a low driving voltage, and luminous efficiency and lifetime.

It is natural that even though the inventive compounds are applied to other organic material layers of an OLED, e.g., an electron injection layer, an electron transport layer, and a hole injection layer as well as a light emitting layer and a hole transport layer, it is possible to achieve the same effects.

Although a preferred embodiment of the present invention has been described for illustrative purposes, those skilled in the art will appreciate that various modifications, additions and substitutions are possible, without departing from the scope and spirit of the invention as disclosed in the accompanying claims. Therefore, the embodiments disclosed in the present invention are intended to illustrate the scope of the technical idea of the present invention, and the scope of the present invention is not limited by the embodiment.

The scope of the present invention shall be construed on the basis of the accompanying claims in such a manner that all of the technical ideas included within the scope equivalent to the claims belong to the present invention.

What is claimed is:

1. A compound represented by one of the Formulas below:

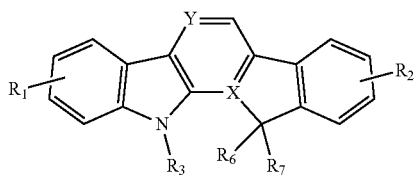

wherein X represents carbon and Y represents carbon or nitrogen, $R_1$ and $R_2$ are the same or different, and each is independently selected from the group consisting of hydrogen, and a substituted or unsubstituted heteroaryl group having 5 to 11 or 13 to 60 nuclear carbon atoms, $R_3$ is selected from the group consisting of hydrogen, a substituted or unsubstituted aryl group having 6 to 24 nuclear carbon atoms, and a substituted or unsubstituted heteroaryl group having 4 to 24 nuclear carbon atoms, and $R_6$ and $R_7$ are the same or different and each is independently selected from the group consisting of hydrogen, unsubstituted phenyl group, and a substituted or unsubstituted alkyl group having 1 to 20 carbon atoms; or

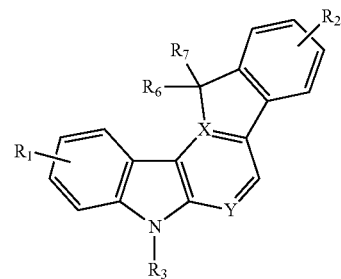

wherein X represents carbon and Y represents carbon or nitrogen, $R_1$ and $R_2$ are the same or different, and each is independently selected from the group consisting of hydrogen, and a substituted or unsubstituted heteroaryl group having 5 to 11 or 13 to 60 nuclear carbon atoms, $R_3$ is selected from the group consisting of hydrogen, a substituted or unsubstituted aryl group having 6 to 24 nuclear carbon atoms, and a substituted or unsubstituted heteroaryl group having 4 to 24 nuclear carbon atoms, and R_6 and R_7 are the same or different and each is independently selected from the group consisting of hydrogen, unsubstituted phenyl, and a substituted or unsubstituted alkyl group having 1 to 20 carbon atoms.

2. The compound as claimed in claim 1, wherein at least one of $R_1$ through $R_3$, $R_6$, and $R_7$ forms a ring together with an adjacent position which is either another $R_1$ through $R_3$, $R_6$, and $R_7$, or pertains to a different group.

3. An organic electronic device comprising one or more organic material layers comprising the compound as claimed in claim 1.

4. The organic electronic device as claimed in claim 3, wherein the organic material layers are formed by a soluble process of the compound.

5. The organic electronic device as claimed in claim 3, wherein the organic electronic device is an organic light emitting device in which a first electrode, said one or more organic material layers, and a second electrode are sequentially layered.

6. The organic electronic device as claimed in claim 5, wherein the organic material layers comprise a light emitting layer, and the compound as claimed in claim 3 is used as a light emitting host material of the light emitting layer.

7. The organic electronic device as claimed in claim 5, wherein the organic material layers comprise a hole transport layer, and the compound as claimed in claim 3 is used for the hole transport layer.

8. The organic electronic device as claimed in claim 5, wherein the organic material layers comprise a hole injection layer, and the compound as claimed in claim 3 is used for the hole injection layer.

9. A terminal comprising a display device and a control part for driving the display device, the display device comprising the organic electronic device as claimed in claim 3.

10. The terminal as claimed in claim 9, wherein the organic electronic device is any one of an organic light emitting device (OLED), an organic solar cell, an organic photo conductor (OPC) drum, an organic transistor (organic TFT), a photodiode, an organic laser, and a laser diode.

11. The organic electronic device as claimed in claim 5, wherein the organic material layers comprise a light emitting layer, and the compound as claimed in claim 3 is used as a light emitting host material of the light emitting layer.

12. The organic electronic device as claimed in claim 5, wherein the organic material layers comprise a hole transport layer, and the compound as claimed in claim 3 is used for the hole transport layer.

13. The organic electronic device as claimed in claim 5, wherein the organic material layers comprise a hole injection layer, and the compound as claimed in claim 3 is used for the hole injection layer.

14. The compound as claimed in claim 1, which is represented by the Formula below:

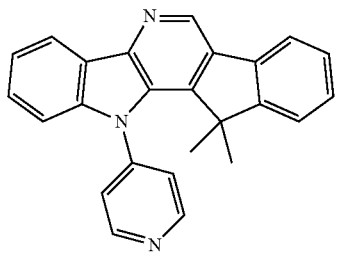

B-5

15. A compound represented by one of the Formulas below,

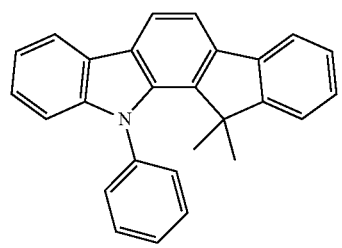

B-1

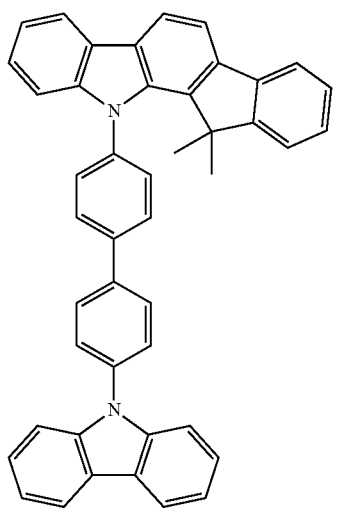

B-2

-continued
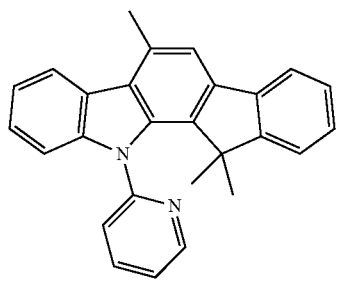
B-3
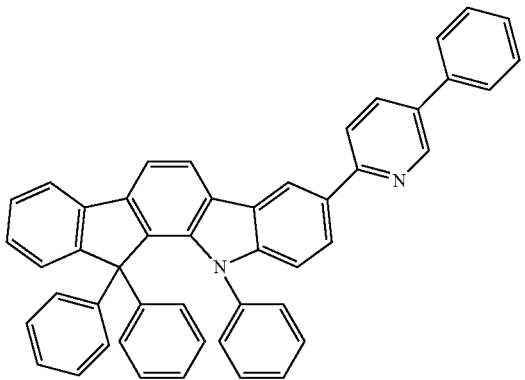
B-4
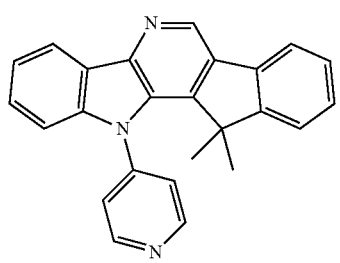
B-5
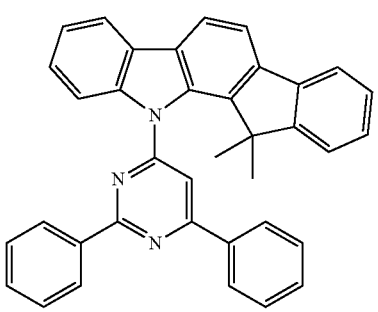
B-7
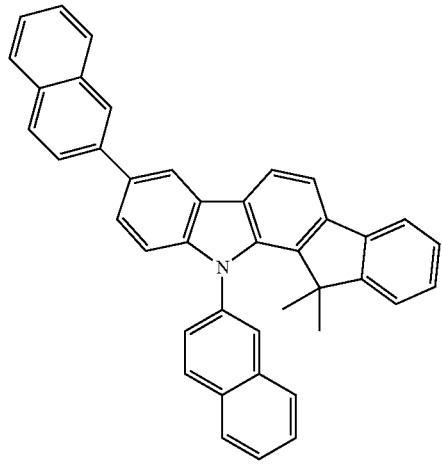
B-8
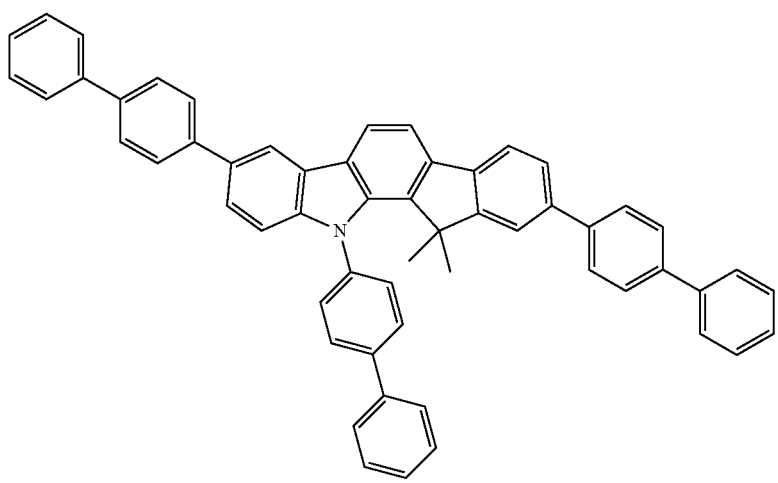
B-9

-continued

B-11

B-12

B-13

B-14

C-1

-continued
C-2
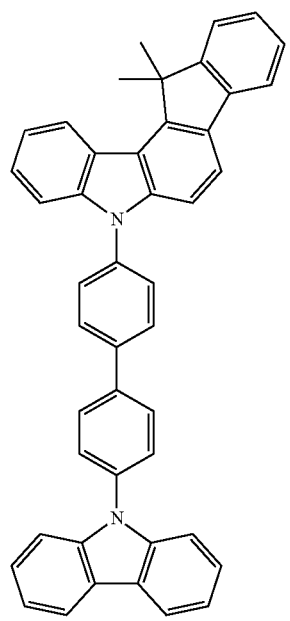
C-3
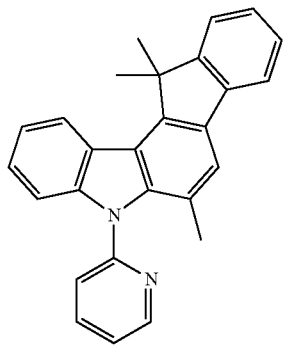
C-4
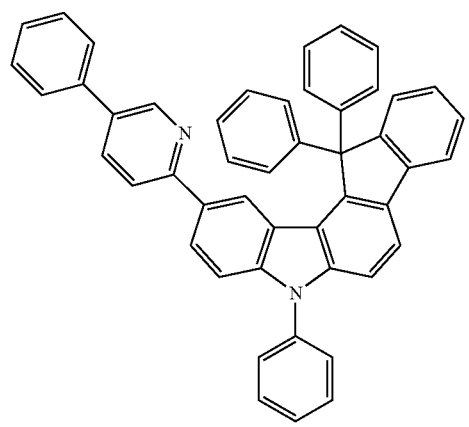
C-6
C-7
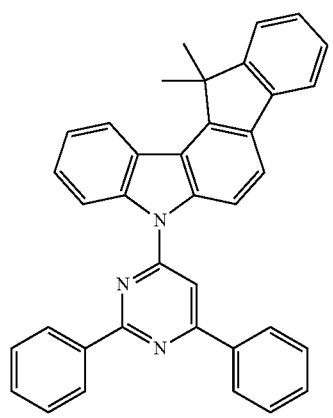
C-8
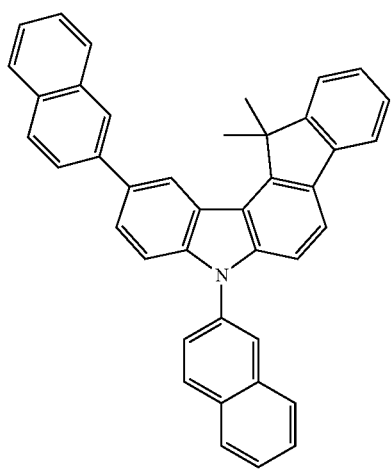

-continued
C-9
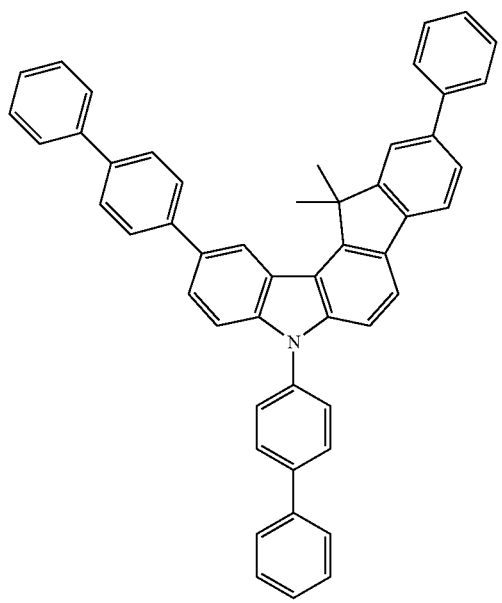
C-11
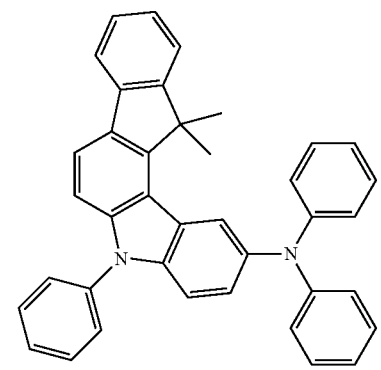
C-12
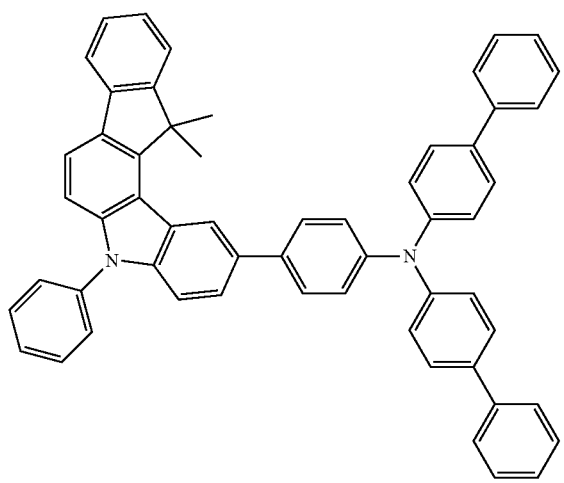
C-13
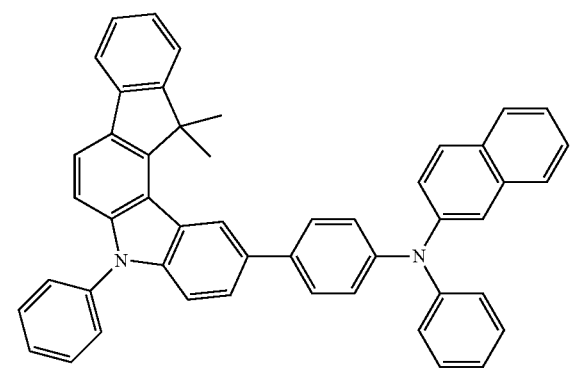
C-14
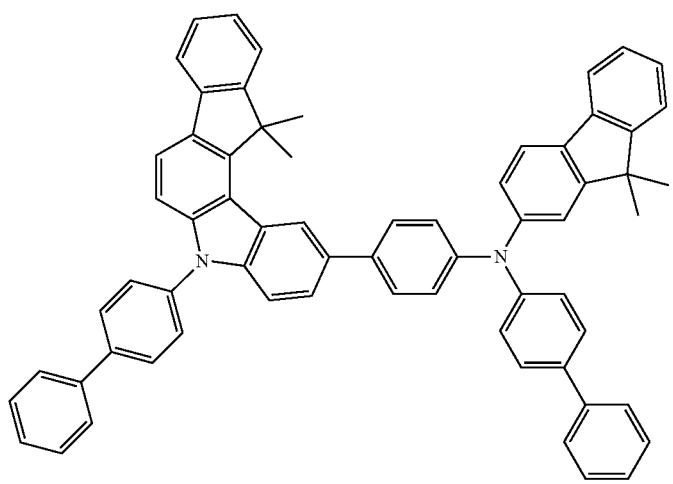

16. An organic electronic device comprising one or more organic material layers comprising a compound as claimed in claim 15.
17. A compound represented by one of the Formulas below,
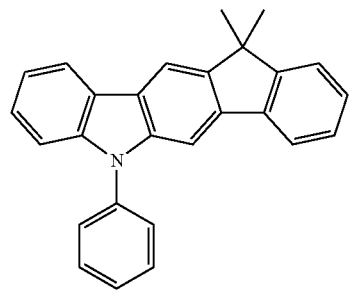
A-1
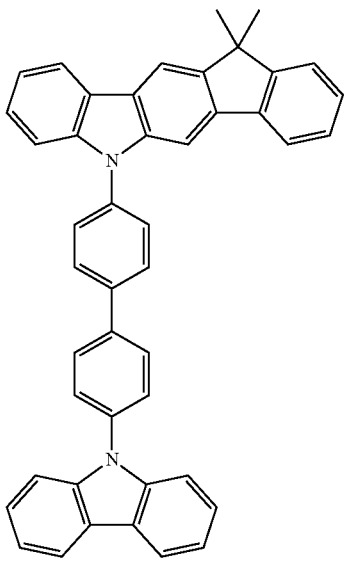
A-2
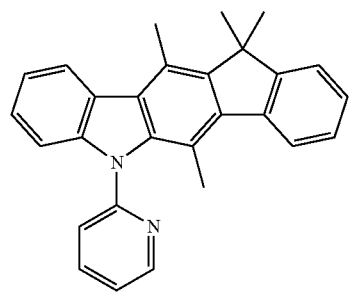
A-3
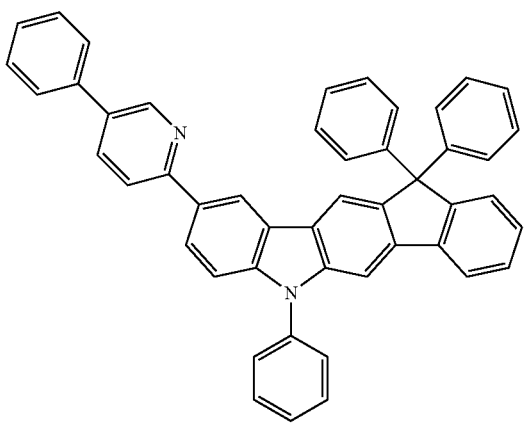
A-4
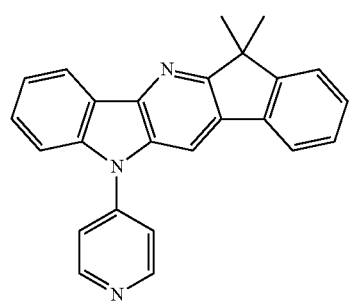
A-5
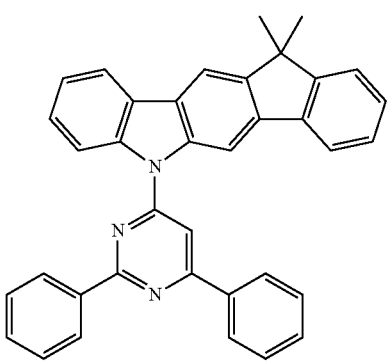
A-7

A-8
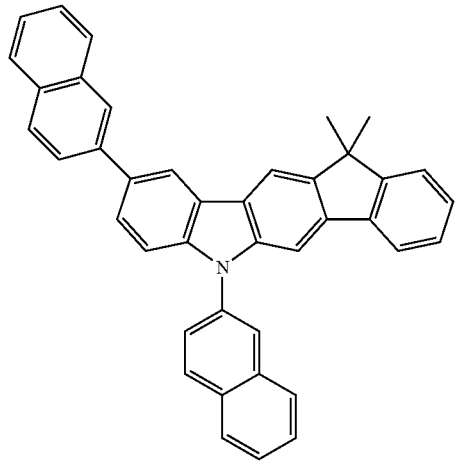
A-9
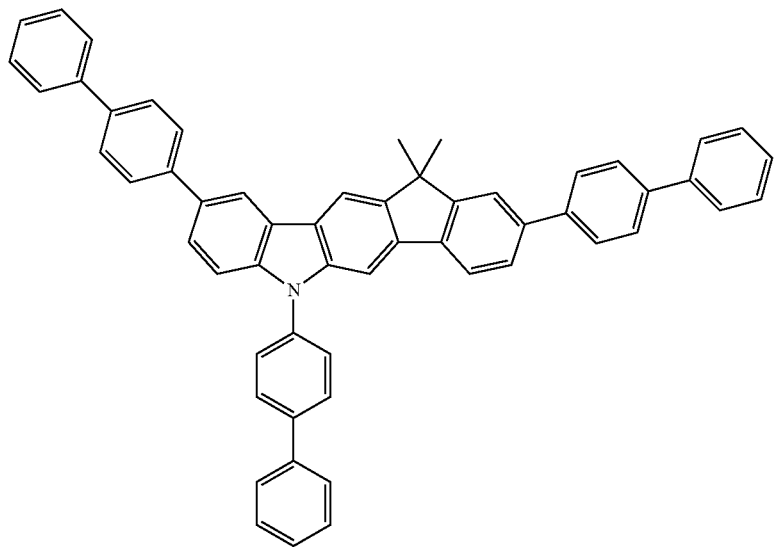
A-11
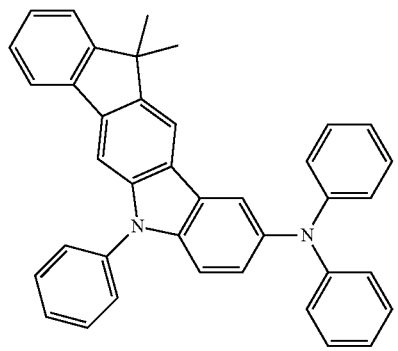
A-12
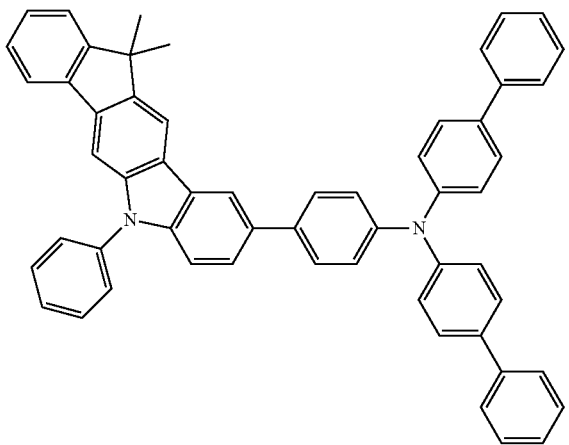

-continued
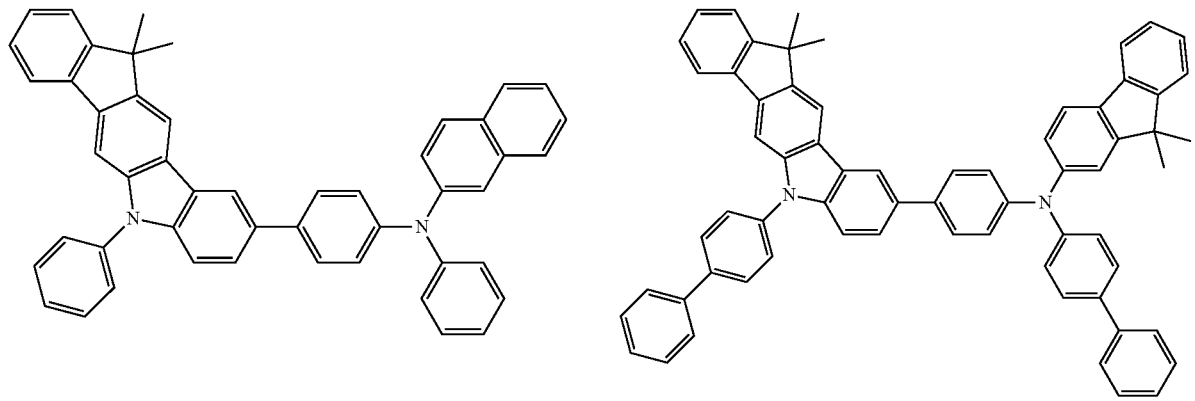
18. The compound as claimed in claim 17, wherein the compound is
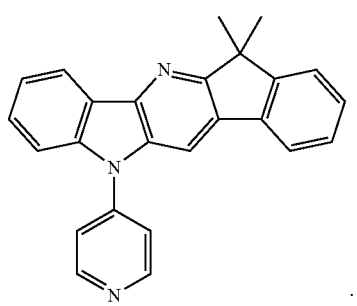
A-5
19. An organic electronic device comprising one or more organic material layers comprising the compound as claimed in claim 17.
* * * * *

UNITED STATES PATENT AND TRADEMARK OFFICE
CERTIFICATE OF CORRECTION

| | | |
|---|---|---|
| PATENT NO. | : 9,233,923 B2 | Page 1 of 1 |
| APPLICATION NO. | : 13/262479 | |
| DATED | : January 12, 2016 | |
| INVENTOR(S) | : Dongha Kim et al. | |

It is certified that error appears in the above-identified patent and that said Letters Patent is hereby corrected as shown below:

Claims

Column 41, Claim 6, Line 24
Please delete "in claim 3 is used"
and replace with -- in claim 1 is used --

Column 41, Claim 7, Line 28
Please delete "in claim 3 is used"
and replace with -- in claim 1 is used --

Column 41, Claim 8, Line 32
Please delete "in claim 3 is used"
and replace with -- in claim 1 is used --

Column 41, Claim 9, Line 36
Please delete "in claim 3."
and replace with -- in claim 1. --

Column 42, Claim 11, Line 7
Please delete "in claim 3 is used"
and replace with -- in claim 1 is used --

Column 42, Claim 12, Line 11
Please delete "in claim 3 is used"
and replace with -- in claim 1 is used --

Column 42, Claim 13, Line 16
Please delete "in claim 3 is used"
and replace with -- in claim 1 is used --

Signed and Sealed this
Fourteenth Day of June, 2016

Michelle K. Lee
*Director of the United States Patent and Trademark Office*